US006121019A

United States Patent [19]
Hillman et al.

[11] Patent Number: 6,121,019
[45] Date of Patent: Sep. 19, 2000

[54] CELL DIVISION REGULATORS

[75] Inventors: Jennifer L. Hillman; Olga Bandman, both of Mountain View; Preeti Lal; Purvi Shah, both of Sunnyvale; Neil C. Corley, Mountain View, all of Calif.

[73] Assignee: Incyte Pharmaceuticals, Inc., Palo Alto, Calif.

[21] Appl. No.: 09/274,570

[22] Filed: Mar. 23, 1999

Related U.S. Application Data

[62] Division of application No. 09/165,234, Oct. 1, 1998, Pat. No. 5,928,899, which is a division of application No. 08/951,148, Oct. 15, 1997, Pat. No. 5,871,973.

[51] Int. Cl.$^7$ .......................... C12N 15/09; C07K 14/435
[52] U.S. Cl. ................ 435/69.1; 435/252.3; 435/252.33; 435/320.1; 530/350; 536/23.1; 536/23.5
[58] Field of Search ................................. 435/69.1, 252.3, 435/252.33, 254.11, 254.3, 325, 410, 320.1; 530/350; 536/23.1, 23.5

[56] References Cited

PUBLICATIONS

Prelich, G. et al., "Functional identity of proliferating cell nuclear antigen and a DNA polymerase–δ auxiliary protein", *Nature*, 326: 517–520.

Coxon, A. et al., "Fission yeast cdc21$^+$ belongs to a family of proteins involved in an early step of chromosome replication", *Nucleic Acids Res.,* 20: 5571–5577 (1992).

Radomski, N. et al., "Molecular Cloning of a Murine cDNA Encoding a Novel Protein, p38–2G4, Which Varies with the Cell Cycle", *Exp. Cell Res.,* 220: 434–445 (1995).

Mori, T. et al., "Isolation and mapping of a human gene (DIFF6) homologous to yeast CDC3, CDC10, CDC11, and mouse Diff6", *Cytogenet. Cell Genet.,* 73: 224–227 (1996).

Longtine, M.S. et al. "The septins: roles in cytokinesis and other processes", *Curr. Opin. Cell Biol.,* 8: 106–119 (1996).

Zieger, B. et al., "Alternative Expression of Platelet Glycoprotein Ibβ mRNA from an Adjacent 5' Gene with an Imperfect Polyadenylation Signal Sequence", *J. Clin. Invest.,* 99: 520–525 (1997).

Nagase, T. et al., "Prediction of the Coding Sequences of Unidentified Human Genes. VI. The Coding Sequences of 80 New Genes (KIAA0201–KIAA0280) Deduced by Analysis of cDNA Clones from Cell Line KG–1 and Brain", *DNA Res.,* 3: 321–329 (1996).

Saraste, M. et al., "The P–loop— a common motif in ATP– and GTP–binding proteins", *Trends Biochem. Sci.,* 15: 430–434 (1990).

Kato, K., (Direct Submission), GenBank Sequence Database (Accession 51203), National Center for Biotechnology Information, National Library of Medicine, Bethesda, Maryland, 20894 (GI 51203) No Date Provided.

Kato, K., (Direct Submission), GenBank Sequence Database (Accession X61452), National Center for Biotechnology Information, National Library of Medicine, Bethesda, Maryland, 20894 (GI 51202) (No Date Provided).

Ware, J. et al., (Direct Submission), GenBank Sequence Database ( Accession 1809317), National Center for Biotechnology Information, National Library of Medicine, Bethesda, Maryland, 20894 (GI 1809317) (No Date Provided).

Ware, J. et al., (Direct Submission), GenBank Sequence Database (Accession U74628), National Center for Biotechnology Information, National Library of Medicine, Bethesda, Maryland, 20894 (GI 1809316) (No Date Provided).

Kato, K., (Direct Submission), GenBank Sequence Database (Accession 1469179), National Center for Biotechnology Information, National Library of Medicine, Bethesda, Maryland, 20894 (GI 1469179) (No Date Provided).

Nagase, T. et al., (Direct Submission), GenBank Sequence Database (Accession D50918), National Center for Biotechnology Information, National Library of Medicine, Bethesda, Maryland, 20894 (GI 1469178) (No Date Provided).

Nakagawa, Y. et al., (Direct Submission), GenBank Sequence Database (Accession 1167967), National Center for Biotechnology Information, National Library of Medicine, Bethesda, Maryland, 20894 (GI 1167967) (No Date Provided).

Nakagawa, Y. et al., (Direct Submission), GenBank Sequence Database (Accession U43918), National Center for Biotechnology Information, National Library of Medicine, Bethesda, Maryland, 20894 (GI 1167966) (No Date Provided).

N–Geneseq Database ACCESSION Q60527, "Human brain Expressed Sequence Tag EST02533", Submitted by Adams et al. (No Date Provided).

Lamartine, J. et al., "Molecular cloning and mapping of human cDNA (PA2G4) that encodes a protein highly homologous to the mouse cell cycle protein p38–2G4", *Cytogenet. Cell Genet.* 78: 31–35 (1997).

*Primary Examiner*—Ponnathapu Achutamurthy
*Assistant Examiner*—Bradley S. Mayhew
*Attorney, Agent, or Firm*—Incyte Pharmaceuticals, Inc.

[57] ABSTRACT

The invention provides three human cell division regulators (HCDR) and polynucleotides which identify and encode HCDR. The invention also provides expression vectors, host cells, agonists, antibodies and antagonists. The invention also provides methods for preventing and treating disorders associated with expression of HCDR.

11 Claims, 26 Drawing Sheets

```
                 9               18              27           36              45              54
5' NNT GGG GTG GGG AAG GAC ATT CCA CAG GCT TTT TTG GCC CCT GCC AGA GAC AGA 63              72              81           90              99              108
   AGG GGG TCA AAG AGA AAG GGA GAG CAA GCC AGG AAG CCA GAC AAC AAC AGC 117             126             135          144             153             162
   ATC AAA ACA AGG CTG TTT CTG TGT GTG AGG AAC TTT GCC TGG GAG ATA AAA TTA 171             180             189          198             207             216
   GAC GAG CTT TCT GAC AGG GAG TCT GAA GCG TGG GAC ATG GAC CGT TCA CTG
                                                        M   D   R   S   L 225             234             243          252             261             270
   GGA TGG CAA GGG AAT TCT GTC CCT GAG GAC AGG ACT GAA GCT GGG ATC AAG CGT
    G   W   Q   G   N   S   V   P   E   D   R   T   E   A   G   I   K   R 279             288             297          306             315             324
   TTC CTG GAG GAC ACG GAT GAT GGA GAA CTG AGC AAG TTC GTG AAG GAT TTC
    F   L   E   D   T   D   D   G   E   L   S   K   F   V   K   D   F 333             342             351          360             369             378
   TCA GGA AAT GCG AGC TGC CAC CCA GAG GCT AAG ACC TGG GCA TCC AGG CCC
    S   G   N   A   S   C   H   P   E   A   K   T   W   A   S   R   P
```

FIGURE 1A

```
CAA GTC CCG GAG CCA AGG CCC CAG GCC CCG GAC CTC TAT GAT GAC CTG GAG
 Q   V   P   E   P   R   P   Q   A   P   D   L   Y   D   D   L   E
387                 396             405             414             423             432

TTC AGA CCC CCC TCG CGG CCC CAG TCC TCT GAC AAC CAG CAG TAC TTC TGT GCC
 F   R   P   P   S   R   P   Q   S   S   D   N   Q   Q   Y   F   C   A
441                 450             459             468             477             486

CCA GCC CCT CTC AGC CCA TCT GCC AGG CCC CGC AGC CCA TGG GGC AAG CTT GAT
 P   A   P   L   S   P   S   A   R   P   R   S   P   W   G   K   L   D
495                 504             513             522             531             540

CCC TAT GAT TCC TCT GAG GAT GAC AAG TCC GTG AAG GAG TAT GGC TTT GTG GGC TTT GCA ACC CTC CCC
 P   Y   D   S   S   E   D   D   K   S   V   K   E   Y   G   F   V   G   F   A   T   L   P
549                 558             567             576             585             594

AAC CAA GTC CAC CGA AAG TCC GTG AAA GGC AAA AAA CTT GGT GCT GAA GAG AGG ATC ATG CAA ACT
 N   Q   V   H   R   K   S   V   K   G   K   K   L   G   A   E   E   R   I   M   Q   T
603                 612             621             630             639             648

GCA GGA GAG TCT GGC CTG GGC AAA CTT GGT GCT GAA GAG AGG ATC ATG CAA ACT
 A   G   E   S   G   L   G   K   L   G   A   E   E   R   I   M   Q   T
657                 666             675             684             693             702

GAT CTG TAC CGG GAC CGG AAA CTT GGT GCT GAA GAG AGG ATC ATG CAA ACT
 D   L   Y   R   D   R   K   L   G   A   E   E   R   I   M   Q   T
711                 720             729             738             747             756
```

FIGURE 1B

```
     765            774            783            792            801            810
GTG GAG ATC ACT AAG CAT GCA GTG GAC ATA GAA GAG AAG GGT GTG AGG CTG CGG
 V   E   I   T   K   H   A   V   D   I   E   E   K   G   V   R   L   R 819            828            837            846            855            864
CTC ACC ATT GTG GAC ACA CCA GGT TTT GGG GAT GCA GTC AAC ACA GAG TGC
 L   T   I   V   D   T   P   G   F   G   D   A   V   N   T   E   C 873            882            891            900            909            918
TGG AAG CCT GTG GCA GAA TAC ATT GAT CAG CAG TTT GAG CAG TAT TTC CGA GAC
 W   K   P   V   A   E   Y   I   D   Q   Q   F   E   Q   Y   F   R   D 927            936            945            954            963            972
GAG AGT GGC CTG AAC CGA AAG AAC ATC CAA GAC AAC AGG GTG CAC TGC TGC CTG
 E   S   G   L   N   R   K   N   I   Q   D   N   R   V   H   C   C   L 981            990            999           1008           1017           1026
TAC TTC ATC TCA CCC TTC GGC CAT GGG CTC CGG CCA TTG GAT GTT GAA TTC ATG
 Y   F   I   S   P   F   G   H   G   L   R   P   L   D   V   E   F   M 1035           1044           1053           1062           1071           1080
AAG GCC CTG CAT CAG CGG GTC AAC ATC GTG CCT ATC CTG GCT AAG GCA GAC ACA
 K   A   L   H   Q   R   V   N   I   V   P   I   L   A   K   A   D   T 1089           1098           1107           1116           1125           1134
CTG ACA CCT CCC GAA GTG GAC CAC AAG AAA CGC AAA ATC CGG GAG GAG ATT GAG
 L   T   P   P   E   V   D   H   K   K   R   K   I   R   E   E   I   E
```

FIGURE 1C

```
                          1143                1152              1161            1170              1179          1188
CAT TTT GGA ATC AAG ATC TAT CAA TTC CCA GAC TGT GAC TCT GAT GAG GAT GAG
 H   F   G   I   K   I   Y   Q   F   P   D   C   D   S   D   E   D   E 1197                1206              1215            1224              1233          1242
GAC TTC AAA TTG CAG GAC CAA GCC CTA AAG GAA AGC ATC CCA TTT GCA GTA ATT
 D   F   K   L   Q   D   Q   A   L   K   E   S   I   P   F   A   V   I 1251                1260              1269            1278              1287          1296
GGC AGC AAC ACT GTA GAG GCC AGA GGG CGG CGA GTT CGG GGT CGA CTC TAC
 G   S   N   T   V   E   A   R   G   R   R   V   R   G   R   L   Y 1305                1314              1323            1332              1341          1350
CCC TGG GGC ATC GTG GAA GTG GAA AAC CCA GGG CAC TGC GAC TTT GTG AAG CTG
 P   W   G   I   V   E   V   E   N   P   G   H   C   D   F   V   K   L 1359                1368              1377            1386              1395          1404
AGG ACA ATG CTG GTA CGT ACC CAC ATG CAG GAC CTG AAG GAT GTG ACA CGG GAG
 R   T   M   L   V   R   T   H   M   Q   D   L   K   D   V   T   R   E 1413                1422              1431            1440              1449          1458
ACA CAT TAT GAG AAC TAC CGG GCA CAG TGC ATC CAG AGC ATG ACC CGC CTG GTG
 T   H   Y   E   N   Y   R   A   Q   C   I   Q   S   M   T   R   L   V 1467                1476              1485            1494              1503          1512
GTG AAG GAA CGG AAT CGC AAC AAA CTG ACT CGG GAA AGT GGT ACC GAC TTC CCC
 V   K   E   R   N   R   N   K   L   T   R   E   S   G   T   D   F   P
```

FIGURE 1D

```
              1521            1530            1539            1548            1557            1566
ATC CCT GCT GTC CCA CCA GGG ACA GAT CCA GAA ACT GAG AAG CTT ATC CGA GAG
 I   P   A   V   P   P   G   T   D   P   E   T   E   K   L   I   R   E 1575            1584            1593            1602            1611            1620
AAA GAT GAG GAG CTG CGG CGG ATG CAG GAG ATG CTA CAC AAA ATA CAA AAA CAG
 K   D   E   E   L   R   R   M   Q   E   M   L   H   K   I   Q   K   Q 1629            1638            1647            1656            1665            1674
ATG AAG GAG AAC TAT TAA CTG GCT TTC AGC CCT GGA TAT TTA AAT CTC CTC CTC
 M   K   E   N   Y 1683            1692            1701            1710            1719            1728
TTC TTC CTG TCC ATG CCG GCC CCT CCC AGC ACC AGC TCT GCT CAG GCC CCT TCA 1737            1746            1755            1764            1773            1782
GCT ACT GCC ACT TCG CCT TAC ATC CCT GCT GAC TGC CCA GAG ACT CAG AGG AAA 1791            1800            1809            1818
TAA AGT TTA ATA AAT CTG TAG GTG GCA AAA AAA AAA  3'
```

```
241 SGLNRKNIQDNRVHCCLYFISPFGHGLRPLDVEFMKALHQ   26459
241 SGLNRKNIQDNRVHCCLYFISPFGHGLRPLDVEFMKALHQ   GI 51203
141 SGLNRKNIQDNRVHCCLYFISPFGHGLRPVDVGFMKALHE   GI 1809317

281 RVNIVPILAKADTLTPPEVDHKKRKIREEIEHFGIKIYQF   26459
281 RVNIVPILAKADTLTPPEVDRKKCKIREEIEHFGIKIYQF   GI 51203
181 KVNIVPLIAKADCLVPSEIRKLKERIREEIDKFGIHVYQF   GI 1809317

321 PDCDSDEDEDFKLQDQALKESIPFAVIGSNTVVEARGRRV   26459
321 PDCDSDEDEDFKLQDQALKESIPFAVIGSNTVVEARGRRV   GI 51203
221 PECDSDEDEDFKQQDRELKESAPFAVIGSNTVVEAKGQRV   GI 1809317

361 RGRLYPWGIVEVENPGHCDFVKLRTMLVRTHMQDLKDVTR   26459
361 RGRLYPWGIVEVENPGHCDFVKLRTMLVRTHMQDLKDVTR   GI 51203
261 RGRLYPWGIVEVENQAHCDFVKLRNMLIRTHMHDLKDVTC   GI 1809317

401 ETHYENYRAQCIQSMTRLVVKERNRNKLTRESGTDFPIPA   26459
401 ETHYENYRAQCIQSMTRLVVKERNRNKLTRESGTDFPIPA   GI 51203
301 DVHYENYRAHCIQQMT-----SKLTQDSRMESPIPI     GI 1809317

441 VP-PGTDPETEKLIREKDEELRRMQEMLHKIQKQMKENY   26459
441 VP-PGTDPETEKLIREKDEELRRMQEMLHKIQRQMKETH   GI 51203
332 LPLPTPDAETEKLIRMKDEELRRMQEMLQRMKQQMQDQ   GI 1809317
```

```
                9          18          27          36          45          54
5' NGA GGC GCG  AGG GAG AGC  CGG AGC CCG  AGC ACT AGC  AGC CGG AGT  CGG 63          72          81          90          99         108
   CGG AAA GCA  CCC GGG CGC  ACG GNA GCA  GCT GCG ATG  GCC GTG GCC
                                                       M   A   V   A 117         126         135         144         153         162
   GTG GGG AGA  CCG TCT AAT  GAA GAG CTT  CGA AAC TTG  TCT TTG TCT  GGC CAT GTG
    V   G   R   P   S   N   E   E   L   R   N   L   S   L   S   G   H   V 171         180         189         198         207         216
   GAC AGC AGC  CTC CCT GAC  CAG CTG GTC  AAC AAG TCT  ACT TCT CAA  GGA TTC
    D   S   S   L   P   D   Q   L   V   N   K   S   T   S   Q   G   F 225         234         243         252         261         270
   TGT TTC AAC  ATC CTT TGT  GTT GGT GAG  ACA GGC ATT  GGC AAA TCC  ACG TTA ATG
    C   F   N   I   L   C   V   G   E   T   G   I   G   K   S   T   L   M 279         288         297         306         315         324
   GAC ACT TTG  TTC AAC ACC  AAA TTT GAA  AGT GAC CCA  GCT ACT CAC  AAT GAA CCA
    D   T   L   F   N   T   K   F   E   S   D   P   A   T   H   N   E   P 333         342         351         360         369         378
   GGT GTT CGG  TTA AAA GCC  AGA AGT TAT  GAG CTT CAG  GAA AGC AAT  GTA CGG CTG
    G   V   R   L   K   A   R   S   Y   E   L   Q   E   S   N   V   R   L
```

```
AAG TTA ACC ATT GTT GAC ACC GTG GGA TTT GGA GAC CAG ATA AAT AAA GAT GAC
 K   L   T   I   V   D   T   V   G   F   G   D   Q   I   N   K   D   D
    387         396         405         414         423         432

AGC TAT AAG CCG ATA GAA TAT ATT GAT GCC CAG TTC GAG GCC TAC CTG CAA
 S   Y   K   P   I   E   Y   I   D   A   Q   F   E   A   Y   L   Q
    441         450         459         468         477         486

GAG GAA TTG AAG ATT AAA CGT TCT CTC TTC AAC TAC CAT GAC ACG AGG ATC CAT
 E   E   L   K   I   K   R   S   L   F   N   Y   H   D   T   R   I   H
    495         504         513         522         531         540

GCC TGC CTC TAC TTT ATT GCC CCT GGA CAT TCA CTA AAG TCC CTG GAT CTG
 A   C   L   Y   F   I   A   P   G   H   S   L   K   S   L   D   L
    549         558         567         576         585         594

GTC ACC ATG AAA AAG CTG GAC AGT AAG GTG AAC ATC ATT CCA ATA ATT GCA AAA
 V   T   M   K   K   L   D   S   K   V   N   I   I   P   I   I   A   K
    603         612         621         630         639         648

GCT GAC ACC ATT GCC AAG AAT GAA CTG CAC AAA TTC AAG AGT AAG ATC ATG AGT
 A   D   T   I   A   K   N   E   L   H   K   F   K   S   K   I   M   S
    657         666         675         684         693         702

GAA CTG GTC AGC AAT GGG GTC CAG ATA TAT CAG TTT CCC ACT GAT GAA GAA ACG
 E   L   V   S   N   G   V   Q   I   Y   Q   F   P   T   D   E   E   T
    711         720         729         738         747         756
```

FIGURE 4B

```
GTG GCA GAG ATT AAC GCA ACA ATG AGT GTC CAT CTC CCA TTT GCA GTG GTT GGC
 V   A   E   I   N   A   T   M   S   V   H   L   P   F   A   V   V   G
765             774             783             792             801     810

AGC ACC GAA GAG GTG CAG AAG ATT GGC AAC AAG ATG GCA AAG GCC AGG CAG TAC CCC
 S   T   E   E   V   Q   K   I   G   N   K   M   A   K   A   R   Q   Y   P
819             828             837             846             855     864

TGG GGT GTG GTG CAG GTT GAG AAT CAT TGC GAT TTT GTG AAA CTT CGA
 W   G   V   V   Q   V   E   N   H   C   D   F   V   K   L   R
873             882             891             900             909     918

GAG ATG CTG ATC CGC AAC ATG GAG GAC TTG CGA GAG CAG CAG TAC ACT CAC ACC CGC
 E   M   L   I   R   N   M   E   D   L   R   E   Q   T   H   T   R
927             936             945             954             963     972

CAC TAT GAA TTG TAC CGA TGT CGC AAG CTT GAA GAG ATG GGG TTC AAG GAC ACT
 H   Y   E   L   Y   R   C   R   K   L   E   E   M   G   F   K   D   T
981             990             999             1008            1017    1026

GAC CCT GAC AGC AAA CCC TTC AGT CTT CAG GAG ACA TAT GAA GCA AAA AGG AAT
 D   P   D   S   K   P   F   S   L   Q   E   T   Y   E   A   K   R   N
1035            1044            1053            1062            1071    1080

GAG TTC CTG GGA GAA CTG CAG AAG AAA GAA GAA ATG GAA AGA CAA ATG TTT GTT
 E   F   L   G   E   L   Q   K   K   E   E   M   E   R   Q   M   F   V
1089            1098            1107            1116            1125    1134
```

FIGURE 4C

```
      1143                  1152              1161              1170              1179              1188
ATG AGA GTG AAG GAG AAA GAA GCT GAA CTT AAG GAG GCA GAG AAA GAG CTT CAC
 M   R   V   K   E   K   E   A   E   L   K   E   A   E   K   E   L   H 1197                  1206              1215              1224              1233              1242
GAG AAG TTT GAC CTT CTA AAG CGG ACA CAC CAA GAA GAA AAG AAA GTG GAA
 E   K   F   D   L   L   K   R   T   H   Q   E   E   K   K   V   E 1251                  1260              1269              1278              1287              1296
GAC AAG AAG GAG CTT GAG GAG GTG GAG AAC TTC CAG AAG AAA GCA
 D   K   K   E   L   E   E   V   E   N   F   Q   K   K   A 1305                  1314              1323              1332              1341              1350
GCG GCT CAG TTA CTA CAG TCC CAG GCC CAG CAA TCT GGG GCC CAG CAA ACC AAG
 A   A   Q   L   L   Q   S   Q   A   Q   Q   S   G   A   Q   Q   T   K 1359                  1368              1377              1386              1395              1404
AAA GAC AAG GAT AAG AAA AAC TGA CCA TCT GCC TCT TGA GAG AGA GAG AAG TGG
 K   D   K   D   K   K   N 1413                  1422              1431              1440              1449              1458
GCA TCC TTC CTT TAA ATT CAG GAA CCA CTG TTG TTT TAT TTG ACT TTT TCT GTT 1467                  1476              1485              1494              1503              1512
ACT TGC ATC CCT TAT ATA AGT TGT TTT GGA TTT GGG ACT ATG TTT TGG GGG AGA
```

FIGURE 4D

```
      1521              1530              1539              1548              1557              1566
AAA ACT CCA GTT AGT TCT GTT TTT TGT ATT GGT TAT TCA GCT TAC TTT TGG TAT 1575              1584              1593              1602              1611              1620
CAA AAT TAT GCC AGT TTT AAG CTC ACT TGA GTG AAG TTT AAG TCA CAA GAT TCT 1629              1638              1647              1656              1665              1674
GTT TAA CAT GCT TTC CTT GTT TTG GAA ACA ACC AAA AAC TTC CCT TTT TTG TTA 1683              1692              1701              1710              1719              1728
CGG GAT TTT GAC CTA CAA ATC ATG TTT AAA ATG TGC CGG TGT TGG GTA 1737              1746              1755              1764              1773              1782
GAT GAC TTT TCT GCC TCT GGG GTT CAA TTT ATA TTT AAA GAT ACC TTA AAA TAA

1791
AAA AAA AAG AAA A 3'
```

FIGURE 4E

```
1    MAVAVGRPSNEELRNLSLSGHVGFDSLPDQLVNKSTSQGF       348429
1    --TDIARQVGEGCRTVPLAGHVGFDSLPDQLVNKSVSQGF       GI 1469179

41   CFNILCVGETGIGKSTLMDTLFNTKFESDPATHNEPGVRL       348429
39   CFNILCVGETGLGKSTLMDTLFNTKFEGEPATHQPGVQL        GI 1469179

81   KARSYELQESNVRLKLTIVDTVGFGDQINKDDSYKPIVEY       348429
79   QSNTYDLQESNVRLKLTIVSTVGFGDQINKEDSYKPIVEF       GI 1469179

121  IDAQFEAYLQEELKIKRSLFNYHDTRIHACLYFIAPTGHS       348429
119  IDAQFEAYLQEELKIRRVLHTYHDSRIHVCLYFIAPTGHS       GI 1469179

161  LKSLDLVTMKKLDSKVNIIPIIAKADTIAKNELHKFKSKI       348429
159  LKSLDLVTMKKLDSKVNIIPIIAKADAISKSELTKFKIKI       GI 1469179

201  MSELVSNGVQIYQFPTDEETVAEINATMSVHLPFAVVGST       348429
199  TSELVSNGVQIYQFPTDDESVAEINGTMNAHLPFAVIGST       GI 1469179

241  EEVKIGNKMAKARQYPWGVVQVENENHCDFVKLREMLIRV       348429
239  EELKIGNKMMRARQYPWGTVQVENEAHCDFVKLREMLIRV       GI 1469179
```

FIGURE 5A

```
281 NMEDLREQTHTRHYELYRRCKLEEMGFKDTDPDSKPFSLQ      348429
279 NMEDLREQTHTRHYELYRRCKLEEMGFKDTDPDSKPFSLQ   GI 1469179

321 ETYEAKRNEFLGELQKKEEEMRQMFVMRVKEKEAELKEAE      348429
319 ETYEAKRNEFLGELQKKEEEMRQMFVQRVKEKEAELKEAE   GI 1469179

361 KELHEKFDLLKRTHQEEKKKVEDKKKELEEEVNNFQKKA       348429
359 KELHEKFDRLKKLHQDEKKKSLDDEVNAFKQRKT         GI 1469179

401 AAQLLQSQAQQQSGAQQT-KKDKDKKN                    348429
399 AAELLQSQGSQAGGSQTLKRDKEKKN                 GI 1469179
```

FIGURE 5B

```
                                                9                18               27               36               45              54
5'     NNT    GCG    CCT    CAG    CCC    GCG    CGC    TCG    CAG    CTT    CTC    GCT    CTC    GCC    TGC    CTG    CCC    GCT 63                                      72               81               90               99              108
       CCC    TTG    CTT    GCT    CGC    GCT    TTC    GCT    CGC    CCT    CTC    GAG    GAT    CTC    CGA    GGG    GAC    TCT 117                                     126              135              144              153              162
       GAC    CAC    AGC    CTG    TGG    CTG    GGA    AGG    GAG    ACA    GAG    GCG    GCT    CAG    GGG    AAA 171                                     180              189              198              207              216
       CGA    GGC    TGC    AGT    GGT    AGT    AGG    ATG    AAG    ATG    TCG    GGC    GAG    GAC    CAA    CAG    GAG
                                                                     M      K      M      S      G      E      D      Q      Q      E 225                                     234              243              252              261              270
       CAA    ACT    ATC    GCT    GAC    CTG    GTC    ACC    AAG    TAT    AAG    ATG    GGG    GGC    GAC    ATC
       Q      T      I      A      D      L      V      T      K      Y      K      M      G      G      D      I 279                                     288              297              306              315              324
       GCC    AAC    AGG    GTA    CTT    CGG    TCC    TTG    GTG    GAA    GCA    TCT    AGC    TCA    GGT    GTG    TCG    GTA
       A      N      R      V      L      R      S      L      V      E      A      S      S      S      G      V      S      V 333                                     342              351              360              369              378
       TTG    AGC    CTG    TGT    GAG    AAA    GGT    GAT    GCC    ATG    ATT    ATG    GAA    GAA    ACA    GGG    AAA    ATC
       L      S      L      C      E      K      G      D      A      M      I      M      E      E      T      G      K      I
```

FIGURE 7A

```
        387         396         405         414         423         432
TTC AAG AAA GAA ATG AAG AAA GGT ATT GCT TTT CCC ACC AGC ATT TCG
 F   K   K   E   M   K   K   G   I   A   F   P   T   S   I   S 441         450         459         468         477         486
GTA AAT TGT GTA TGT CAC TTC TCC CCT TTG AAG AGC GAC CAG GAT TAT ATT
 V   N   C   V   C   H   F   S   P   L   K   S   D   Q   D   Y   I 495         504         513         522         531         540
CTC AAG GAA GGT GAC TTG GTA AAA ATT GAC CTT GGG GTC CAT GTG GAT GGC TTC
 L   K   E   G   D   L   V   K   I   D   L   G   V   H   V   D   G   F 549         558         567         576         585         594
ATC GCT AAT GTA GCT CAC ACT TTT GTT GTG GTA GCT CAG GGG ACC CAA GTA
 I   A   N   V   A   H   T   F   V   V   V   A   Q   G   T   Q   V 603         612         621         630         639         648
ACA GGG AGG AAA GCA GAT GTT ATT AAG GCA GCT CAC CTT TGT GCT GAA GCT GCC
 T   G   R   K   A   D   V   I   K   A   A   H   L   C   A   E   A   A 657         666         675         684         693         702
CTA CGC CTG GTC AAA CCT GGA AAT CAG AAC ACA CAA GTG ACA GAA GCC TGG AAC
 L   R   L   V   K   P   G   N   Q   N   T   Q   V   T   E   A   W   N 711         720         729         738         747         756
AAA GTT GCC CAC TCA TTT AAC TGC ACG CCA ATA GAA GGT ATG CTG TCA CAC CAG
 K   V   A   H   S   F   N   C   T   P   I   E   G   M   L   S   H   Q
```

FIGURE 7B

```
       765                774                783        792                801                810
TTG AAG CAG CAT GTC GAT GGA GAA AAA ACC ATT ATC CAG AAT CCC ACA GAC
 L   K   Q   H   V   D   G   E   K   T   I   I   Q   N   P   T   D 819                828                837        846                855                864
CAG AAG AAG GAC CAT GAA AAA GCT GAA TTT GAG GTA CAT GAA GTA TAT GCT
 Q   K   K   D   H   E   K   A   E   F   E   V   H   E   V   Y   A 873                882                891        900                909                918
GTG GAT GTT CTC GTC AGC TCA GGA GAG GGC AAG GAT GCA GGA CAG AGA
 V   D   V   L   V   S   S   G   E   G   K   D   A   G   Q   R 927                936                945        954                963                972
ACC ATT TAC AAA CGA GAC CCC TCT AAA CAG TAT GGA CTG AAA ATG AAA ACT
 T   I   Y   K   R   D   P   S   K   Q   Y   G   L   K   M   K   T 981                990                999        1008               1017               1026
TCA CGT GCC TTC TTC AGT GAG GTG GAA AGG CGT TTT GAT GCC ATG CCG TTT ACT
 S   R   A   F   F   S   E   V   E   R   R   F   D   A   M   P   F   T 1035               1044               1053       1062               1071               1080
TTA AGA GCA TTT GAA GAT GAG AAG AAG GCT CGG ATG GGT GTG GAG TGC GCC
 L   R   A   F   E   D   E   K   K   A   R   M   G   V   V   E   C   A 1089               1098               1107       1116               1125               1134
AAA CAT GAA CTG CTG CAA CCA TTT AAT GTT CTC TAT GAG AAG GGT GAA TTT
 K   H   E   L   L   Q   P   F   N   V   L   Y   E   K   G   E   F
```

FIGURE 7C

```
         1143            1152            1161            1170            1179            1188
GTT GCC CAG TTT AAA TTT ACA GTT CTG CTC ATG CCC AAT GGC CCC ATG CGG ATA
 V   A   Q   F   K   F   T   V   L   L   M   P   N   G   P   M   R   I 1197            1206            1215            1224            1233            1242
ACC AGT GGT CCC TTC GAG CCT GAC CTC TAC AAG CTC TAT GAG ATG GAG GTC CAG GAT
 T   S   G   P   F   E   P   D   L   Y   K   S   E   M   E   V   Q   D 1251            1260            1269            1278            1287            1296
GCA GAG AAG CTA GCC CTC CTC CAG AGT TCT GCA AGT CGA AAA ACC CAG AAA AAG
 A   E   K   L   A   L   L   Q   S   S   A   S   R   K   T   Q   K   K 1305            1314            1323            1332            1341            1350
AAA AAA AAG AAG GCC TCC AAG ACT GCA GAG AAT GCC ACC AGT GGG GAA ACA TTA
 K   K   K   K   A   S   K   T   A   E   N   A   T   S   G   E   T   L 1359            1368            1377            1386            1395            1404
GAA GAA AAT GAA GCT GGG GAC TGA GGT GGG TCC CAT CTC CCC AGC TTG CTG CTC
 E   E   N   E   A   G   D 1413            1422            1431            1440            1449            1458
CTG CCT CAT CCC CTT CCC ACC ATA CCC CAG ACT CTG TGA AGG CAG TTT TTC TCC    3'
```

FIGURE 7D

|  | 2458438 | GI 1167967 |
|---|---|---|
| 1  MSGEDEQQEQTIAEDLVVTKYKMGGDIANRVLRSLVEASS | | |
| 1  MSGEDEQQEQTIAEDLVVTKYKMGGDIANRVLRSLVEASS | | |
| 41 SGVSVLSLCEKGDAMIMEETGKIFKKEKEMKKGIAFPTSI | | |
| 41 SGVSVLSLCEKGDAMIMEETGKIFKKEKEMKKGIAFPTSI | | |
| 81 SVNNCVCHFSPLKSDQDYILKEGDLVKIDLGVHVDGFIAN | | |
| 81 SVNNCVCHFSPLKSDQDYILKEGDLVKIDLGVHVDGFIAN | | |
| 121 VAHTFVVDVAQGTQVTGRKADVIKAAAHLCAEAALRLVKPG | | |
| 121 VAHTFVIGVAQGTQVTGRKADVIKAAHLCAEAALRLVKPG | | |
| 161 NQNTQVTEAWNKVAHSFNCTPIEGMLSHQLKQHVIDGEKT | | |
| 161 NQNTQVTEAWNKVAHSFNCTPIEGMLSHQLKQHVIDGEKT | | |
| 201 IIQNPTDQQKKDHEKAEFEVHEVYAVDVLVSSGEGKAKDA | | |
| 201 IIQNPTDQQKKDHEKAEFEVHEVYAVDVLVSSGEGKAKDA | | |
| 241 GQRTTIYKRDPSKQYGLKMKTSRAFFSEVERRFDAMPFTL | | |
| 241 GQRTTIYKRDPSKQYGLKMKTSRAFFSEVERRFDAMPFTL | | |

CELL DIVISION REGULATORS

This application is a divisional of U.S. application Ser. No. 09/165,234, filed Oct. 1, 1998, now U.S. Pat. No. 5,928,899, which is a divisional of U.S. application Ser. No. 08/951,148, filed Oct. 15, 1997, now U.S. Pat. No. 5,871,973.

FIELD OF THE INVENTION

This invention relates to nucleic acid and amino acid sequences of three new human cell division regulators and to the use of these sequences in the diagnosis, prevention, and treatment of inflammation and disorders associated with cell proliferation and apoptosis.

BACKGROUND OF THE INVENTION

Cell division is the fundamental process by which living organisms grow and reproduce. The cycle of cell division consists of three principle events: interphase, mitosis, and cytokinesis. During interphase, replication of the DNA and production of essential proteins are synthesized. In mitosis, the nuclear material is divided and separated to opposite halves of the cell. In cytokinesis, the cell cytoplasm is divided. These cell cycle events are regulated by various cell division regulators.

A group of cell division regulatory proteins active in the interphase is related to nuclear redistribution and modulation. These regulatory proteins include the proliferating cell nuclear antigen (PCNA) which is identified as the DNA polymerase-δ auxiliary protein (Prelich, G. et al. (1987) Nature 326: 517–520), the *Schizosaccharomyces pombe* Cdc21p gene (Coxon, A. et al. (1992) Nucleic Acids Res. 20: 5571–5577), and a murine cell cycle-specifically modulated nuclear protein, p38-2G4 (Radomski, N. and Jost, E. (1995) Exp. Cell Res. 220: 434–445). p38-2G4 is a nuclear protein of 38 kDa and is a murine homolog of *S. pombe* Cdc21p gene product. p38-2G4 shows its highest expression between the G1 phase and the mid S phase and contains a number of putative phosphorylation sites, a cryptic nuclear localization signal, and an amphipathic helical domain.

The process of cytokinesis and septum formation has been well studied. Cytokinesis is believed to be mediated by the filaments and other components formed from GTP-binding proteins (Mori, et al. (1996) Cytogenet. Cell Genet. 73: 224–227). Septins are a family of proteins that are involved in septum formation. (Longtine, M. S. et al. (1996) Curr. Opin. Cell Biol. 8:106–119). In yeast, four gene products (CDC3, CDC10, CDC11, and CDC12) are members of this family and are associated with the "bud filament" which is located directly inside the cytoplasmic membrane. Mutations in any of the CDC genes disrupts cytokinesis and gives rise to multi-nucleated cells with abnormal bud growth.

Homologs of the yeast septins have been found in *Drosophila melanogaster* (Sep2), mouse (H5; proliferation associated protein 1; Nakagawa, Y. et al. (1996) unpublished), and human (KIAA0128; cell division control related protein; Zieger, B. et al. (1997) J. Clin. Invest. 99: 520–525; Nagase, T. et al. (1996) DNA Res. 3: 321–329). Most of these proteins share three domains rich in basic amino acids that are a common motif of GTP-binding proteins and of the GTPase superfamily. The first of these three domains, the sequence GXXGXGKST, is thought to be an ATP/GTP-binding site (P-loop) that may be involved in septin assembly or function (Saraste, M. et al. (1990) Trends Biochem. Sci. 15:430–34). Most of the known septins also contain predicted coiled-coil domains of 35 to 98 amino acids near the C-termini (Longtine et al., supra). These domains may be involved in homotypic or heterotypic interactions among the septins themselves and/or with other proteins.

The discovery of three new human cell division regulators and the polynucleotides encoding them satisfies a need in the art by providing new compositions which are useful in the diagnosis, prevention, and treatment of inflammation and disorders associated with cell proliferation and apoptosis.

SUMMARY OF THE INVENTION

The invention features three substantially purified polypeptides, designated individually as HCDR-1, HCDR-2, and HCDR-3, and collectively as HCDR, having the amino acid sequences shown in SEQ ID NO:1, SEQ ID NO:3, and SEQ ID NO:5.

The invention further provides an isolated and substantially purified polynucleotide sequence encoding the polypeptide HCDR-1, comprising the amino acid sequence of SEQ ID NO:1 or fragments thereof and compositions comprising said polynucleotide sequence. The invention also provides a polynucleotide sequence which hybridizes under stringent conditions to the polynucleotide sequence encoding the amino acid sequence SEQ ID NO:1 or fragments of said polynucleotide sequence. The invention further provides a polynucleotide sequence comprising the complement of the polynucleotide sequence encoding the amino acid sequence of SEQ ID NO:1, or fragments or variants of said polynucleotide sequence.

The invention also provides an isolated and purified sequence comprising SEQ ID NO:2, or variants thereof. In addition, the invention provides a polynucleotide sequence which hybridizes under stringent conditions to the polynucleotide sequence of SEQ ID NO:2. The invention also provides a polynucleotide sequence comprising the complement of SEQ ID NO:2, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:1, or a fragment thereof, the method comprising the steps of: a) culturing the host cell containing an expression vector containing at least a fragment of the polynucleotide sequence encoding HCDR-1 under conditions suitable for the expression of the polypeptide; and b) recovering the polypeptide from the host cell culture.

The invention also provides a pharmaceutical composition comprising a substantially purified HCDR-1 having the amino acid sequence of SEQ ID NO:1 in conjunction with a suitable pharmaceutical carrier.

The invention also provides a purified antagonist of the polypeptide of SEQ ID NO:1. In one aspect the invention provides a purified antibody which binds to a polypeptide comprising the amino acid sequence of SEQ ID NO:1.

Still further, the invention provides a purified agonist of the polypeptide of SEQ ID NO:1.

The invention also provides a method for stimulating cell proliferation comprising administering to a cell an effective amount of purified HCDR-1.

The invention also provides a method for preventing or treating a disorder associated with an increase in apoptosis comprising administering to a subject in need of such treatment an effective amount of a pharmaceutical composition comprising purified HCDR-1.

The invention also provides a method for preventing or treating a cancer comprising administering to a subject in need of such treatment an effective amount of an antagonist of HCDR-1.

The invention also provides a method for preventing or treating an inflammation comprising administering to a subject in need of such treatment an effective amount of an antagonist of HCDR-1.

The invention also provides a method for detecting a polynucleotide which encodes HCDR-1 in a biological sample comprising the steps of: a) hybridizing the complement of the polynucleotide sequence which encodes SEQ ID NO:1 to nucleic acid material of a biological sample, thereby forming a hybridization complex; and b) detecting the hybridization complex, wherein the presence of the complex correlates with the presence of a polynucleotide encoding HCDR-1 in the biological sample. In one aspect the nucleic acid material of the biological sample is amplified by the polymerase chain reaction prior to hybridization.

Still further, the invention provides an isolated and substantially purified polynucleotide sequence encoding the polypeptide HCDR-2, comprising the amino acid sequence of SEQ ID NO:3 or fragments thereof and compositions comprising said polynucleotide sequence. The invention also provides a polynucleotide sequence which hybridizes under stringent conditions to the polynucleotide sequence encoding the amino acid sequence SEQ ID NO:3 or fragments of said polynucleotide sequence. The invention further provides a polynucleotide sequence comprising the complement of the polynucleotide sequence encoding the amino acid sequence of SEQ ID NO:3, or fragments or variants of said polynucleotide sequence.

The invention also provides an isolated and purified sequence comprising SEQ ID NO:4, or variants thereof. In addition, the invention provides a polynucleotide sequence which hybridizes under stringent conditions to the polynucleotide sequence of SEQ ID NO:4. The invention also provides a polynucleotide sequence comprising the complement of SEQ ID NO:4, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:3, or a fragment thereof, the method comprising the steps of: a) culturing the host cell containing an expression vector containing at least a fragment of the polynucleotide sequence encoding HCDR-2 under conditions suitable for the expression of the polypeptide; and b) recovering the polypeptide from the host cell culture.

The invention also provides a pharmaceutical composition comprising a substantially purified HCDR-2 having the amino acid sequence of SEQ ID NO:3 in conjunction with a suitable pharmaceutical carrier.

The invention also provides a purified antagonist of the polypeptide of SEQ ID NO:3. In one aspect the invention provides a purified antibody which binds to a polypeptide comprising the amino acid sequence of SEQ ID NO:3.

Still further, the invention provides a purified agonist of the polypeptide of SEQ ID NO:3.

The invention also provides a method for stimulating cell proliferation comprising administering to a cell an effective amount of purified HCDR-2.

The invention also provides a method for preventing or treating a disorder associated with an increase in apoptosis comprising administering to a subject in need of such treatment an effective amount of a pharmaceutical composition comprising purified HCDR-2.

The invention also provides a method for preventing or treating a cancer comprising administering to a subject in need of such treatment an effective amount of an antagonist of HCDR-2.

The invention also provides a method for preventing or treating an inflammation comprising administering to a subject in need of such treatment an effective amount of an antagonist of HCDR-2.

The invention also provides a method for detecting a polynucleotide which encodes HCDR-2 (SEQ ID NO:3) in a biological sample comprising the steps of: a) hybridizing the complement of the polynucleotide sequence which encodes SEQ ID NO:3 to nucleic acid material of a biological sample, thereby forming a hybridization complex; and b) detecting the hybridization complex, wherein the presence of the complex correlates with the presence of a polynucleotide encoding HCDR-2 in the biological sample. In one aspect the nucleic acid material of the biological sample is amplified by the polymerase chain reaction prior to hybridization.

Still further, the invention provides an isolated and substantially purified polynucleotide sequence encoding the polypeptide HCDR-3, comprising the amino acid sequence of SEQ ID NO:5 or fragments thereof and compositions comprising said polynucleotide sequence. The invention also provides a polynucleotide sequence which hybridizes under stringent conditions to the polynucleotide sequence encoding the amino acid sequence SEQ ID NO:5 or fragments of said polynucleotide sequence. The invention further provides a polynucleotide sequence comprising the complement of the polynucleotide sequence encoding the amino acid sequence of SEQ ID NO:5, or fragments or variants of said polynucleotide sequence.

The invention also provides an isolated and purified sequence comprising SEQ ID NO:6, or variants thereof. In addition, the invention provides a polynucleotide sequence which hybridizes under stringent conditions to the polynucleotide sequence of SEQ ID NO:6. The invention also provides a polynucleotide sequence comprising the complement of SEQ ID NO:6, or fragments or variants thereof.

The present invention further provides an expression vector containing at least a fragment of any of the claimed polynucleotide sequences. In yet another aspect, the expression vector containing the polynucleotide sequence is contained within a host cell.

The invention also provides a method for producing a polypeptide comprising the amino acid sequence of SEQ ID NO:5, or a fragment thereof, the method comprising the steps of: a) culturing the host cell containing an expression vector containing at least a fragment of the polynucleotide sequence encoding HCDR-3 under conditions suitable for the expression of the polypeptide; and b) recovering the polypeptide from the host cell culture.

The invention also provides a pharmaceutical composition comprising a substantially purified HCDR-3 having the amino acid sequence of SEQ ID NO:5 in conjunction with a suitable pharmaceutical carrier.

The invention also provides a purified antagonist of the polypeptide of SEQ ID NO:5. In one aspect the invention provides a purified antibody which binds to a polypeptide comprising the amino acid sequence of SEQ ID NO:5.

Still further, the invention provides a purified agonist of the polypeptide of SEQ ID NO:5.

The invention also provides a method for stimulating cell proliferation comprising administering to a cell an effective amount of purified HCDR-3.

The invention also provides a method for preventing or treating a disorder associated with an increase in apoptosis comprising administering to a subject in need of such treatment an effective amount of a pharmaceutical composition comprising purified HCDR-3.

The invention also provides a method for preventing or treating a cancer comprising administering to a subject in need of such treatment an effective amount of an antagonist of HCDR-3.

The invention also provides a method for preventing or treating an inflammation comprising administering to a subject in need of such treatment an effective amount of an antagonist of HCDR-3.

The invention also provides a method for detecting a polynucleotide which encodes HCDR-3 in a biological sample comprising the steps of: a) hybridizing the complement of the polynucleotide sequence which encodes SEQ ID NO:5 to nucleic acid material of a biological sample, thereby forming a hybridization complex; and b) detecting the hybridization complex, wherein the presence of the complex correlates with the presence of a polynucleotide encoding HCDR-3 in the biological sample. In one aspect the nucleic acid material of the biological sample is amplified by the polymerase chain reaction prior to hybridization.

BRIEF DESCRIPTION OF THE FIGURES

FIGS. 1A, 1B, 1C, 1D, and 1E show the amino acid sequence (SEQ ID NO:1) and nucleic acid sequence (SEQ ID NO:2) of HCDR-1. The alignment was produced using MacDNASIS PRO™ software (Hitachi Software Engineering Co. Ltd. San Bruno, Calif.).

FIGS. 2A and 2B show the amino acid sequence alignments among HCDR-1 (26459; SEQ ID NO:1), a mouse H5 protein (GI 51203; SEQ ID NO:7), and a human cell division control related protein (GI 1809317; SEQ ID NO:8), produced using the multisequence alignment program of LASERGENE software (DNASTAR Inc, Madison Wis.).

FIGS. 4A, 4B, 4C, 4D, and 4E show the amino acid sequence (SEQ ID NO:3) and nucleic acid sequence (SEQ ID NO:4) of HCDR-2. The alignment was produced using MacDNASIS PRO™ software (Hitachi Software Engineering Co. Ltd. San Bruno, Calif.).

FIGS. 5A and 5B show the amino acid sequence alignments between HCDR-2 (348429; SEQ ID NO:3) and a human homolog of CDC10, KIAA0128 (GI 1469179; SEQ ID NO:9), produced using the multisequence alignment program of LASERGENE software (DNASTAR Inc, Madison Wis.).

FIGS. 7A, 7B, 7C, and 7D show the amino acid sequence (SEQ ID NO:5) and nucleic acid sequence (SEQ ID NO:6) of HCDR-3. The alignment was produced using MacDNASIS PRO™ software (Hitachi Software Engineering Co. Ltd. San Bruno, Calif.).

FIGS. 8A and 8B show the amino acid sequence alignments between HCDR-3 (2458438; SEQ ID NO:5) and a mouse proliferation-associated protein 1 (GI 1167967; SEQ ID NO:10), produced using the multisequence alignment program of LASERGENE software (DNASTAR Inc, Madison Wis.).

DESCRIPTION OF THE INVENTION

Figure 3A:
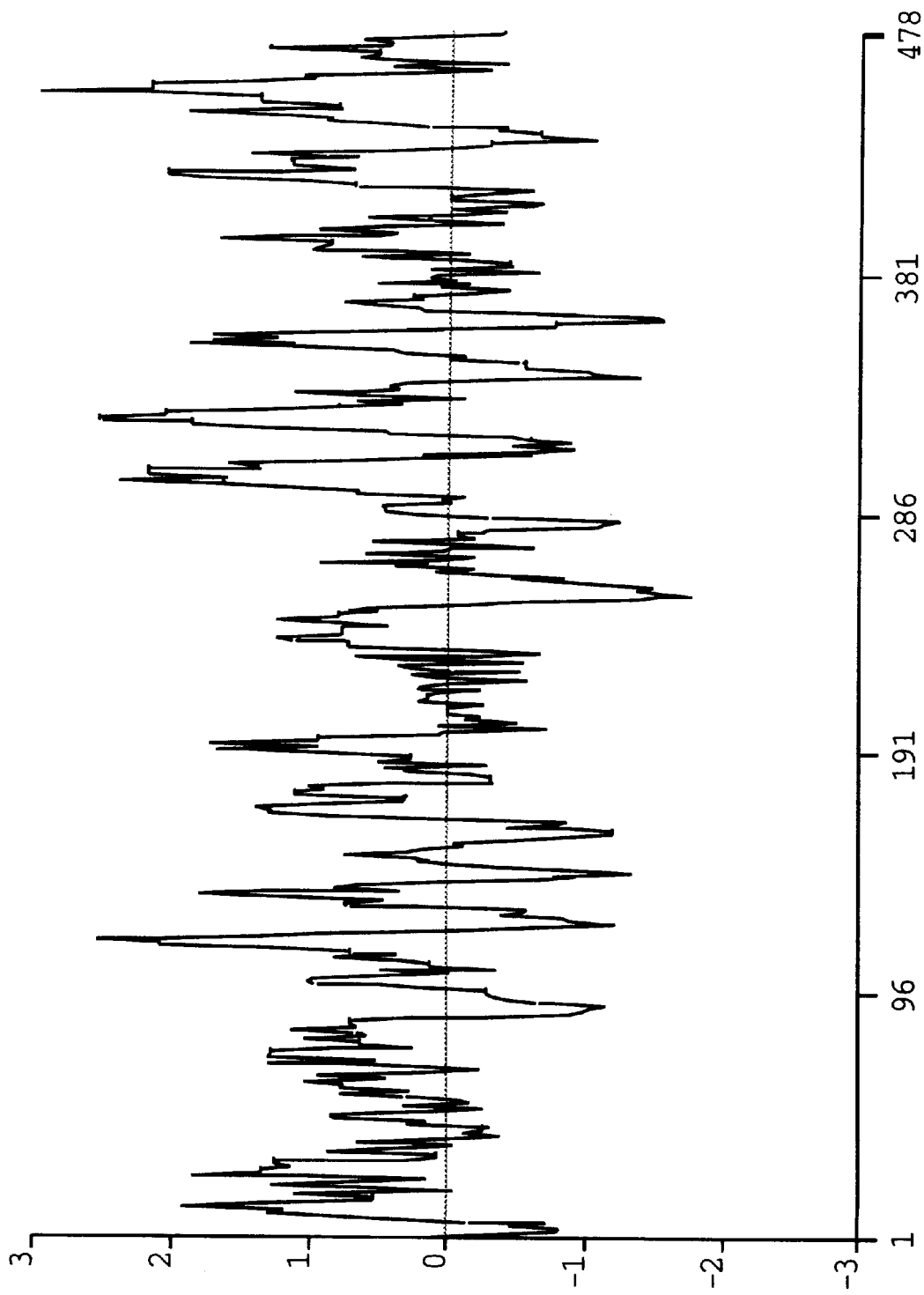
FIGS. 3A and 3B show the hydrophobicity plots for HCDR-1 (SEQ ID NO:1) and the mouse H5 protein (SEQ ID NO:7), respectively. The positive X axis reflects amino acid position, and the negative Y axis, hydrophobicity (MacDNASIS PRO software).

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

HCDR, as used herein, refers to the amino acid sequences of substantially purified HCDR obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to HCDR, increases or prolongs the duration of the effect of HCDR. Agonists may include proteins, nucleic acids, carbohydrates, or any other molecules which bind to and modulate the effect of HCDR.

An "allele" or "allelic sequence", as used herein, is an alternative form of the gene encoding HCDR. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HCDR as used herein include those with deletions, insertions, or substitutions of different nucleotides resulting in a polynucleotide that encodes the same or a functionally equivalent HCDR. Included within this definition are polymorphisms which may or may not be readily detectable using a particular oligonucleotide probe of the polynucleotide encoding HCDR, and improper or unexpected hybridization to alleles, with a locus other than the normal chromosomal locus for the polynucleotide sequence encoding HCDR. The encoded protein may also be "altered" and contain deletions, insertions, or substitutions of amino acid residues which produce a silent change and result in a functionally equivalent HCDR. Deliberate amino acid substitutions may be made on the basis of similarity in polarity, charge, solubility, hydrophobicity, hydrophilicity, and/or the amphipathic nature of the residues as long as the biological or immunological activity of HCDR is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of HCDR are preferably about 5 to about 15 amino acids in length and retain the biological activity or the immunological activity of HCDR. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual*, Cold Spring Harbor Press, Plainview, N.Y.).

The term "antagonist" as used herein, refers to a molecule which, when bound to HCDR, decreases the amount or the duration of the effect of the biological or immunological activity of HCDR. Antagonists may include proteins, nucleic acids, carbohydrates, antibodies or any other molecules which decrease the effect of HCDR.

As used herein, the term "antibody" refers to intact molecules as well as fragments thereof, such as Fa, F(ab')$_2$, and Fv, which are capable of binding the epitopic determinant. Antibodies that bind HCDR polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic HCDR, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding HCDR (SEQ ID NO:1, SEQ ID NO:3, or SEQ ID NO:5) or fragments thereof (e.g., SEQ ID NO:2, SEQ ID NO:4, SEQ ID NO:6 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR (Perkin Elmer, Norwalk, Conn.) in the 5' and/or the 3' direction and resequenced, or has been assembled from the overlapping sequences of more than one Incyte Clone using a computer program for fragment assembly (e.g., GEL VIEW Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID NO:2, SEQ ID NO:4, or SEQ ID NO:6 by northern analysis is indicative of the presence of mRNA encoding HCDR in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to HCDR or the encoded HCDR. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target sequence.

Human artificial chromosomes (HACs) are linear microchromosomes which may contain DNA sequences of 10K to 10M in size and contain all of the elements required for stable mitotic chromosome segregation and maintGenet. (Harrington, J. J. et al. (1997) Nat Genet. 15:345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of HCDR. For example, modulation may cause an increase or a decrease in protein activity, binding characteristics, or any other biological, functional or immunological properties of HCDR.

"Nucleic acid sequence" as used herein, refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8:53–63).

The term "portion", as used herein, with regard to a protein (as in "a portion of a given protein") refers to fragments of that protein. The fragments may range in size from five amino acid residues to the entire amino acid sequence minus one amino acid. Thus, for example, a protein "comprising at least a portion of the amino acid sequence of SEQ ID NO:1" encompasses the full-length HCDR-1 and fragments thereof.

The term "sample", as used herein, is used in its broadest sense. A biological sample suspected of containing nucleic acid encoding HCDR, or fragments thereof, or HCDR itself may comprise a bodily fluid, extract from a cell, chromosome, organelle, or membrane isolated from a cell, a cell, genomic DNA, RNA, or cDNA (in solution or bound to a solid support, a tissue, a tissue print, and the like).

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of HCDR, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, LASERGENE software.

The Invention

The invention is based on the discovery of three new human cell division regulators (hereinafter collectively referred to as "HCDR"), the polynucleotides encoding HCDR, and the use of these compositions for the diagnosis, prevention, or treatment of inflammation and disorders associated with cell proliferation and apoptosis.

Nucleic acids encoding the HCDR-1 of the present invention were first identified in Incyte Clone 26459 from a fetal spleen tissue cDNA library (SPLNFET01) using a computer search for amino acid sequence alignments. A consensus sequence, SEQ ID NO:2, was derived from the following overlapping and/or extended nucleic acid sequences: Incyte Clones 26459 (SPLNFET01), 100469 (ADRENOT01), and 240018 (HIPONOT01).

Figure 2A:
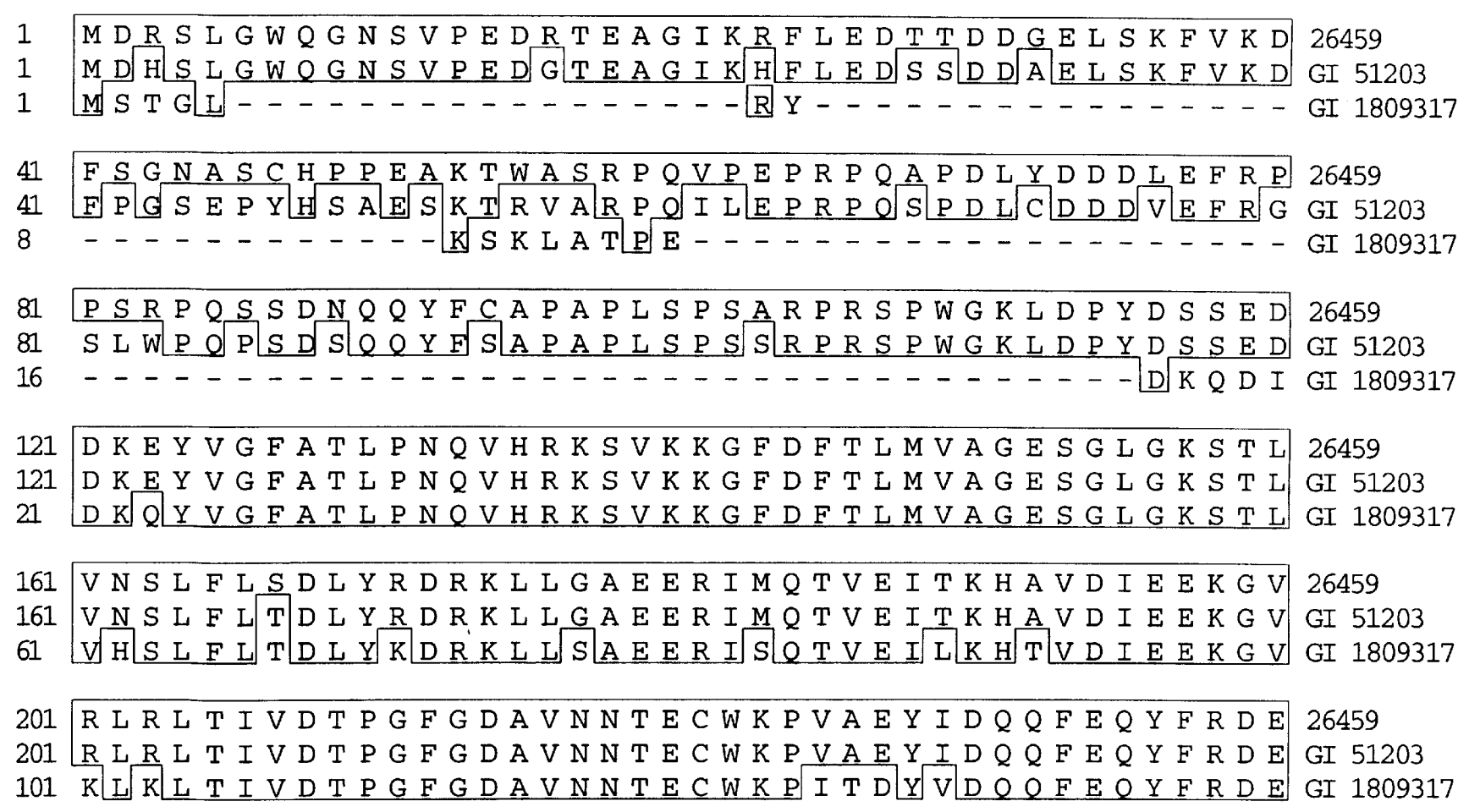
Figure 3B:
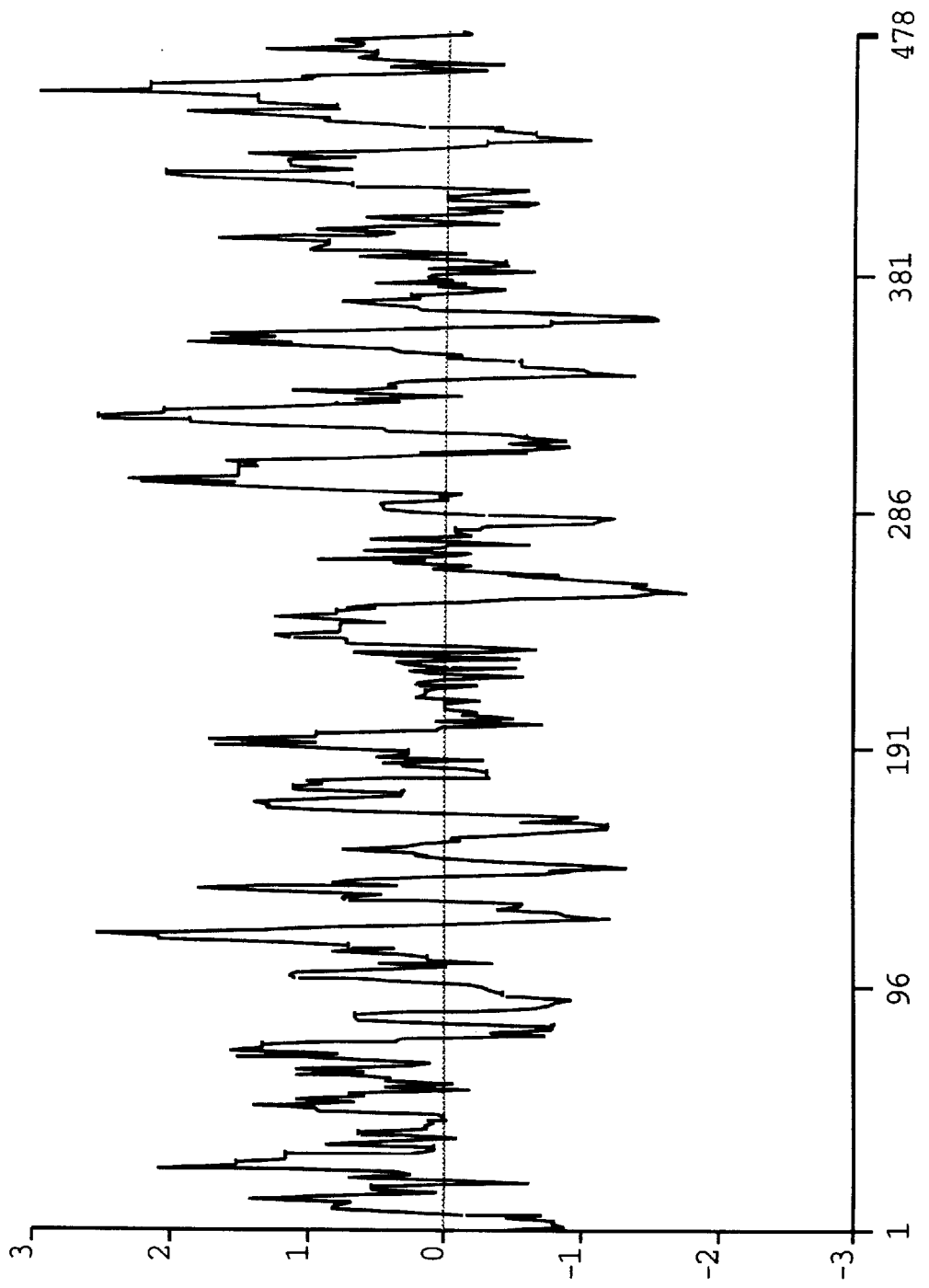

In one embodiment, the invention encompasses a polypeptide, HCDR-1, comprising the amino acid sequence of SEQ ID NO:1, as shown in FIGS. 1A, 1B, 1C, 1D, and 1E. HCDR-1 is 478 amino acids in length. It has a conserved ATP/GTP-binding site encompassing residues G151-S158, analogous to other identified septins. HCDR-1 has one potential amidation site encompassing residues R356-R359; two potential N-glycosylation sites encompassing residues N44-C47 and N217-E220; 11 potential casein kinase II phosphorylation sites encompassing residues S11-E14, T28-D31, S117-D120, S118-D121, T205-D208, T295-E298, S325-D328, T351-E354, T402-E405, S432-D435, and T445-E448; and three potential protein kinase C phosphorylation sites encompassing residues S102-R104, S138-K140, and T449-K451. As shown in FIGS. 2A and 2B, HCDR-1 has chemical and structural homology with a mouse H5 protein (GI 51203; SEQ ID NO:7) and a human cell division control related protein (GI 1809317; SEQ ID NO:8). In particular, HCDR-1 and the mouse H5 protein share 92% sequence homology, HCDR-1 and the human cell division control related protein share 80% sequence homology. As illustrated by FIGS. 3A and 3B, HCDR-1 and the mouse H5 protein have rather similar hydrophobicity plots. Northern analysis shows the expression of HCDR-1 in various cDNA libraries, at least 34% of which are immortalized or cancerous, at least 20% of which involve immune response, and at least 14% are expressed in fetal/infant tissues or organs.

Nucleic acids encoding the HCDR-2 of the present invention were first identified in Incyte Clone 348429 from a ventricle tissue cDNA library (LVENNOT01) using a computer search for amino acid sequence alignments. A consensus sequence, SEQ ID NO:4, was derived from the following overlapping and/or extended nucleic acid sequences: Incyte Clones 407765 (EOSIHET02), 2265406 (UTRSNOT02), and 348429 (LVENNOT01).

Figure 6A:
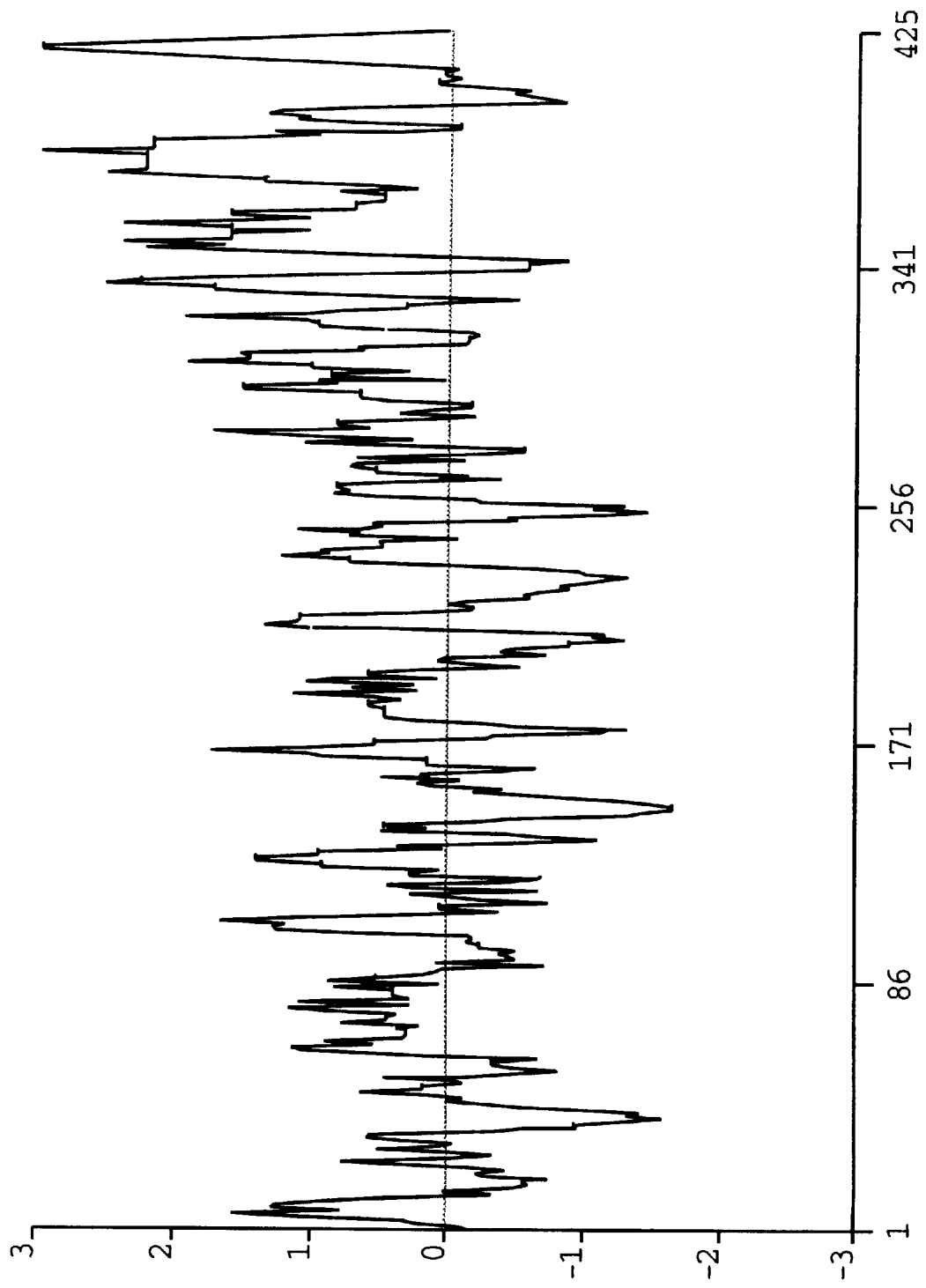
FIGS. 6A and 6B show the hydrophobicity plots for HCDR-2 (SEQ ID NO:3) and KIAA0128 (SEQ ID NO:9), respectively. The positive X axis reflects amino acid position, and the negative Y axis, hydrophobicity (MacDNASIS PRO software).
Figure 6B:
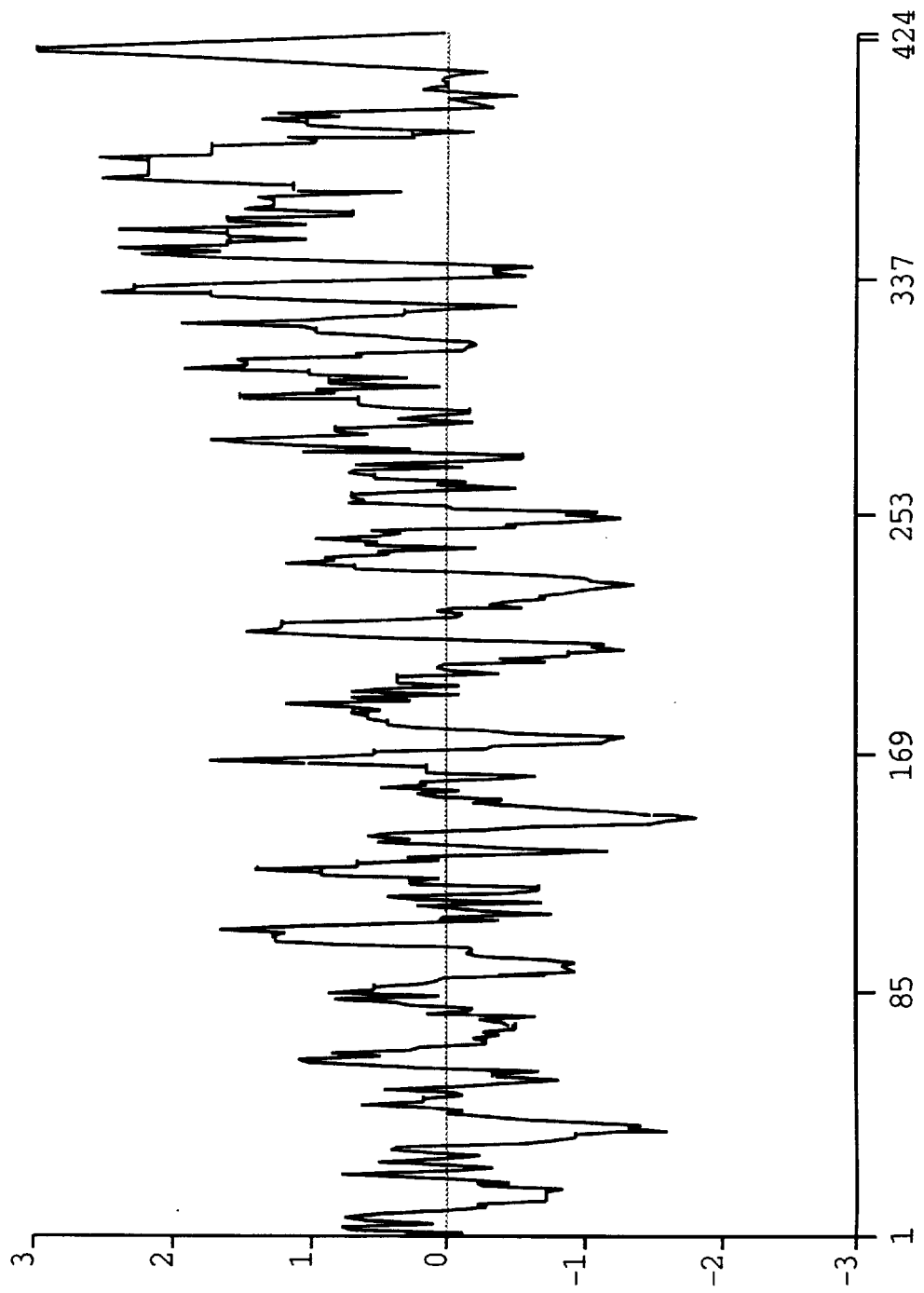

In one embodiment, the invention encompasses a polypeptide, HCDR-2, comprising the amino acid sequence of SEQ ID NO:3, as shown in FIGS. 4A, 4B, 4C, 4D, and 4E. HCDR-2 is 425 amino acids in length. It has a conserved ATP/GTP-binding site encompassing residues G48-S55. HCDR-2 has three potential N-glycosylation sites encompassing residues N15-L18, N33-T36, and N225-M228; 13 potential casein kinase II phosphorylation sites encompassing residues S9-E12, S26-D29, T56-D59, T64-E67, T72-E75, T97-D100, T216-E219, T220-E223, S239-E242, T310-D313, S318-E321, T373-E376, and T417-D420; and four potential protein kinase C phosphorylation sites encompassing residues S113-K115, S160-K162, T168-K170, and T417-K419. As shown in FIGS. 5A and 5B, HCDR-2 has chemical and structural homology with a human CDC10-related protein, KIAA0128 (GI 1469179; SEQ ID NO:9). In particular, HCDR-2 and KIAA0128 share 82% sequence homology. As illustrated by FIGS. 6A and 6B, HCDR-2 and KIAA0128 have rather similar hydrophobicity plots. Northern analysis shows the expression of HCDR-2 in various cDNA libraries, at least 38% of which are immortalized or cancerous, at least 14% of which involve immune response, and at least 24% are expressed in fetal/infant tissues or organs.

Nucleic acids encoding the HCDR-3 of the present invention were first identified in Incyte Clone 2458438 from a aortic endothelial cell cDNA library (ENDANOT01) using a computer search for amino acid sequence alignments. A consensus sequence, SEQ ID NO:6, was derived from the following overlapping and/or extended nucleic acid sequences: Incyte Clones 1287508 (BRAINOT11), 1747368

(STOMTUT02), 2636947 (BONTNOT01), 2635478 (BONTNOT01), 2325889 (OVARNOT02), and 2458438 (ENDANOT01).

Figure 9A:
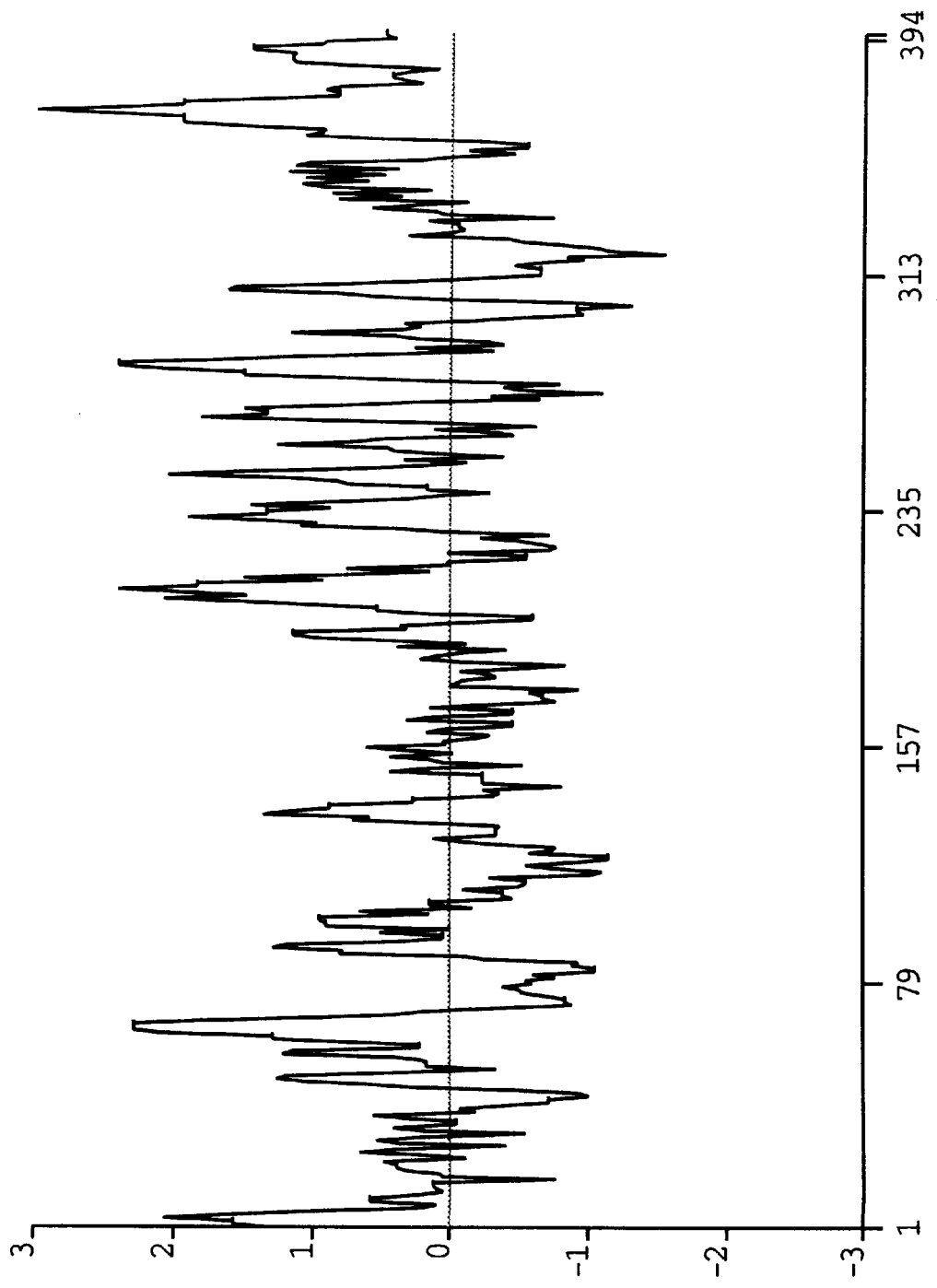
FIGS. 9A and 9B show the hydrophobicity plots for HCDR-3 (SEQ ID NO:5) and the mouse proliferation-associated protein 1 (SEQ ID NO:9), respectively. The positive X axis reflects amino acid position, and the negative Y axis, hydrophobicity (MacDNASIS PRO software).
Figure 9B:
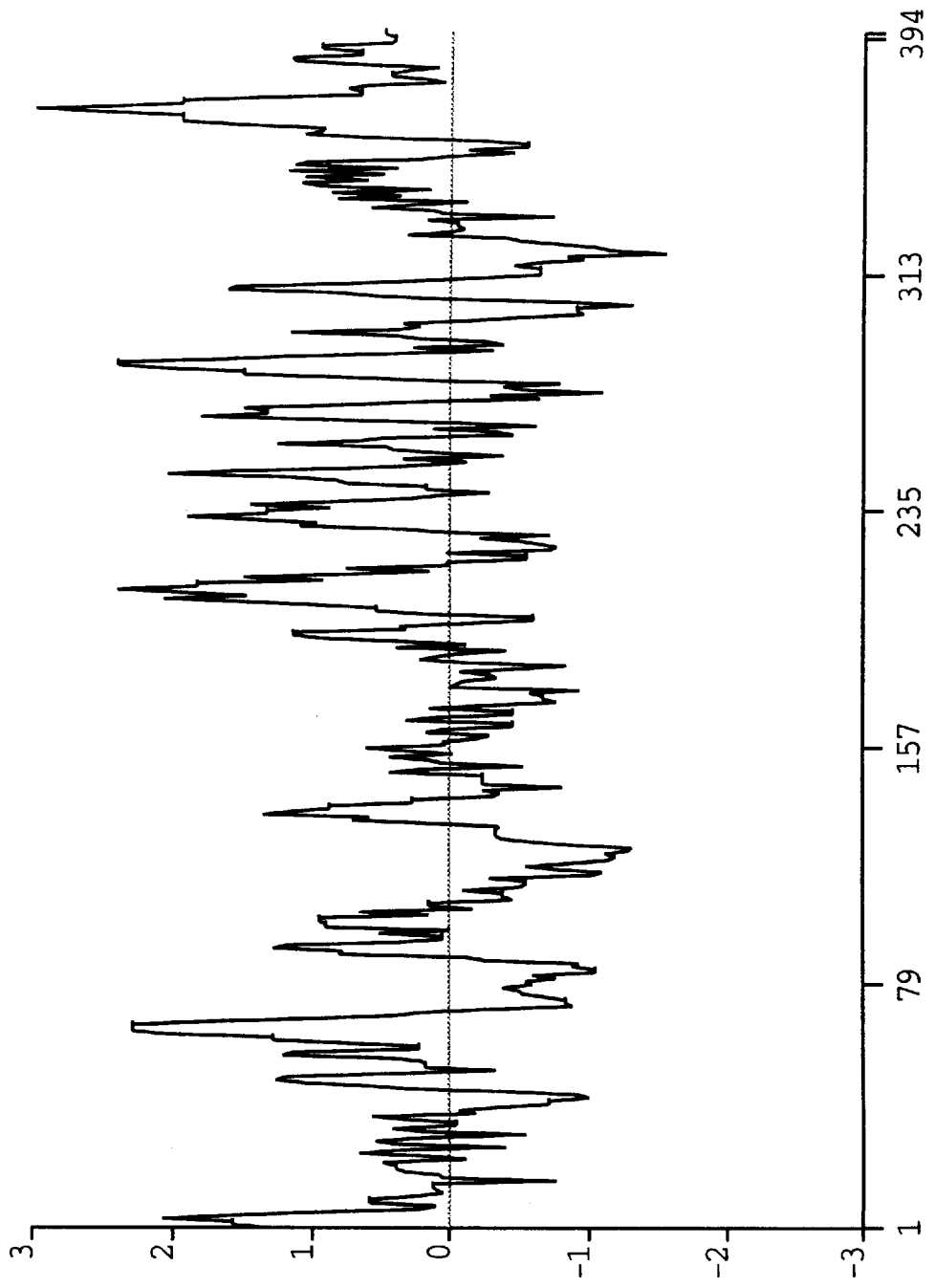

In one embodiment, the invention encompasses a polypeptide, HCDR-3, comprising the amino acid sequence of SEQ ID NO:5, as shown in FIGS. 7A, 7B, 7C, and 7D. HCDR-3 is 417 amino acids in length. HCDR-3 has one potential amidation site encompassing residues T136-K139; one potential N-glycosylation site encompassing residues N380-S383; one potential cAMP- and cGMP-dependent protein kinase phosphorylation site encompassing residues K372-S375; 11 potential casein kinase II phosphorylation sites encompassing residues S2-D5, T11-E14, S34-E37, S47-E50, S94-D97, T180-E183, S231-E234, S267-E270, S345-E348, T382-E385, and T386-E389; and six potential protein kinase C phosphorylation sites encompassing residues T60-K62, T136-R138, T261-R263, T279-R281, S363-K365, and T366-K369. As shown in FIGS. 8A and 8B, HCDR-3 has chemical and structural homology with mouse proliferation-associated protein 1 (GI 1167967; SEQ ID NO:10). In particular, HCDR and the mouse proliferation-associated protein 1 share 98% sequence homology. As illustrated by FIGS. 9A and 9B, HCDR-3 and the mouse protein have rather similar hydrophobicity plots. Northern analysis shows the expression of HCDR-3 in various cDNA libraries, at least 59% of which are immortalized or cancerous, at least 19% of which involve immune response, and at least 23% are expressed in fetal/infant tissues or organs.

The invention also encompasses HCDR variants. A preferred HCDR variant is one having at least 80%, and more preferably at least 90%, amino acid sequence identity to the HCDR amino acid sequence (SEQ ID NO:1, SEQ ID NO:3, or SEQ ID NO:5) and which retains at least one biological, immunological or other functional characteristic or activity of HCDR. A most preferred HCDR variant is one having at least 95% amino acid sequence identity to SEQ ID NO:1, SEQ ID NO:3, or SEQ ID NO:5.

The invention also encompasses polynucleotides which encode HCDR. Accordingly, any nucleic acid sequence which encodes the amino acid sequence of HCDR can be used to produce recombinant molecules which express HCDR. In a particular embodiment, the invention encompasses the polynucleotide comprising the nucleic acid sequence of SEQ ID NO:2, SEQ ID NO:4, or SEQ ID NO:6 as shown, respectively, in FIGS. 1A, 1B, 1C, 1D, and 1E; FIGS. 4A, 4B, 4C, 4D; and 4E, or FIGS. 7A, 7B, 7C, and 7D.

It will be appreciated by those skilled in the art that as a result of the degeneracy of the genetic code, a multitude of nucleotide sequences encoding HCDR, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HCDR, and all such variations are to be considered as being specifically disclosed.

Although nucleotide sequences which encode HCDR and its variants are preferably capable of hybridizing to the nucleotide sequence of the naturally occurring HCDR under appropriately selected conditions of stringency, it may be advantageous to produce nucleotide sequences encoding HCDR or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HCDR and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode HCDR and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HCDR or any fragment thereof.

Also encompassed by the invention are polynucleotide sequences that are capable of hybridizing to the claimed nucleotide sequences, and, in particular, those shown in SEQ ID NO:2, SEQ ID NO:4, or SEQ ID NO:6, under various conditions of stringency as taught in Wahl, G. M. and S. L. Berger (1987; Methods Enzymol. 152:399–407) and Kimmel, A. R. (1987; Methods Enzymol. 152:507–511).

Methods for DNA sequencing which are well known and generally available in the art and may be used to practice any of the embodiments of the invention. The methods may employ such enzymes as the Klenow fragment of DNA polymerase I, Sequenase® (U.S. Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding HCDR may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HCDR may be used in recombinant DNA molecules to direct expression of HCDR, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HCDR.

As will be understood by those of skill in the art, it may be advantageous to produce HCDR-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HCDR encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HCDR may be ligated to a heterologous sequence to encode a fusion protein. For example, to screen peptide libraries for inhibitors of HCDR activity, it may be useful to encode a chimeric HCDR protein that can be recognized by a commercially available antibody. A fusion protein may also be engineered to contain a cleavage site located between the HCDR encoding sequence and the heterologous protein sequence, so that HCDR may be cleaved and purified away from the heterologous moiety.

In another embodiment, sequences encoding HCDR may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HCDR, or a fragment thereof For example, peptide synthesis can be performed using various solid-phase techniques (Roberge, J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of HCDR, or any part thereof, may be altered during direct synthesis and/or combined using chemical methods with sequences from other proteins, or any part thereof, to produce a variant polypeptide.

In order to express a biologically active HCDR, the nucleotide sequences encoding HCDR or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HCDR and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express sequences encoding HCDR. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HCDR, vectors based on SV40 or EBV may be used with an appropriate selectable marker.

In bacterial systems, a number of expression vectors may be selected depending upon the use intended for HCDR. For example, when large quantities of HCDR are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the sequence encoding HCDR may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of sequences encoding HCDR may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; and Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express HCDR. For example, in one such system, *Autographa californica* nuclear polyhedrosis virus (AcNPV) is used as a vector to express foreign genes in *Spodoptera frugiperda* cells or in Trichoplusia larvae. The sequences encoding HCDR may be cloned into a non-essential region of the virus, such as the polyhedrin gene, and placed under control of the polyhedrin promoter. Successful insertion of HCDR will render the polyhedrin gene inactive and produce recombinant virus lacking coat protein. The recombinant viruses may then be used to infect, for example, *S. frugiperda* cells or Trichoplusia larvae in which HCDR may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, sequences encoding HCDR may be ligated into an adenovirus transcription/translation complex consisting of the late promoter and tripartite leader sequence. Insertion in a non-essential E1 or E3 region of the viral genome may be used to obtain a viable virus which is capable of expressing HCDR in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery methods (liposomes, polycationic amino polymers, or vesicles) for therapeutic purposes.

Specific initiation signals may also be used to achieve more efficient translation of sequences encoding HCDR. Such signals include the ATG initiation codon and adjacent sequences. In cases where sequences encoding HCDR, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeLa, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express HCDR may be transformed using expression vectors which may contain viral origins of replication and/or endogenous expression elements and a selectable marker gene on the same or on a separate vector.

Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides, neomycin and G-418 (Colbere-Garapin, F. et al (1981) J. Mol. Biol. 150:1–14); and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confined. For example, if the sequence encoding HCDR is inserted within a marker gene sequence, transformed cells containing sequences encoding HCDR can be identified by the absence of marker gene function. Alternatively, a marker gene can be placed in tandem with a sequence encoding HCDR under the control of a single promoter. Expression of the marker gene in response to induction or selection usually indicates expression of the tandem gene as well.

Alternatively, host cells which contain the nucleic acid sequence encoding HCDR and express HCDR may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding HCDR can be detected by DNA-DNA or DNA-RNA hybridization or amplification using probes or fragments or fragments of polynucleotides encoding HCDR. Nucleic acid amplification based assays involve the use of oligonucleotides or oligomers based on the sequences encoding HCDR to detect transformants containing DNA or RNA encoding HCDR.

A variety of protocols for detecting and measuring the expression of HCDR, using either polyclonal or monoclonal antibodies specific for the protein are known in the ar Examples include enzyme-linked immunosorbent assay (ELISA), radiommunoassay (RIA), and fluorescence activated cell sorting (FACS). A two-site, monoclonal-based immunoassay utilizing monoclonal antibodies reactive to two non-interfering epitopes on HCDR is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HCDR include oligolabeling, nick translation, end-labeling or PCR amplification using a labeled nucleotide. Alternatively, the sequences encoding HCDR, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Mich.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding HCDR may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HCDR may be designed to contain signal sequences which direct secretion of HCDR through a prokaryotic or eukaryotic cell membrane. Other constructions may be used to join sequences encoding HCDR to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HCDR may be used to facilitate purification. One such expression vector provides for expression of a fusion protein containing HCDR and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif. 3: 263–281) while the enterokinase cleavage site provides a means for purifying HCDR from the fusion protein. A discussion of vectors which contain fusion proteins is provided in Kroll, D. J. et al. (1993; DNA Cell Biol. 12:441–453).

In addition to recombinant production, fragments of HCDR may be produced by direct peptide synthesis using solid-phase techniques Merrifield J. (1963) J. Am. Chem. Soc. 85:2149–2154). Protein synthesis may be performed using manual techniques or by automation. Automated synthesis may be achieved, for example, using Applied Biosystems 431A Peptide Synthesizer (Perkin Elmer). Various fragments of HCDR may be chemically synthesized separately and combined using chemical methods to produce the full length molecule.

Therapeutics

Chemical and structural homology exists among HCDR-1, a mouse H5 protein (GI 51203; SEQ ID NO:7), and a human cell division control related protein (GI 1809317; SEQ ID NO:8); between HCDR-2 and a human CDC10-related protein, KIAA0128 (GI 1469179; SEQ ID NO:9); and between HCDR-3 and mouse proliferation-associated protein 1 (GI 1167967; SEQ ID NO:10). Northern analysis shows that the expression of HCDR (SEQ ID NO:1, SEQ ID NO:3, or SEQ ID NO:5) is associated with cancer and fetal/infant development. Therapeutic uses for all three polypeptides are described collectively below.

During fetal development, decreased expression of HCDR may cause an increase in apoptosis with no adverse effects to the subject. However, in other situations and in adults, decreased expression of HCDR may cause an increase in apoptosis which is detrimental. Therefore, in one embodiment, HCDR or a fragment or derivative thereof may be administered to a subject to prevent or treat a disorder associated with an increase in apoptosis. Such disorders include, but are not limited to, AIDS and other infectious or genetic immunodeficiencies, neurodegeaerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis.

In another embodiment, a pharmaceutical composition comprising HCDR may be administered to a subject to prevent or treat a disorder associated with increased apoptosis including, but not limited to, those listed above.

In still another embodiment, an agonist which is specific for HCDR may be administered to prevent or treat a disorder associated with increased apoptosis including, but not limited to, those listed above.

In still another embodiment, a vector capable of expressing HCDR, or a fragment or a derivative thereof, may be used to prevent or treat a disorder associated with increased apoptosis-including, but not limited to, those listed above.

In a further embodiment, HCDR or a fragment or derivative thereof may be added to cells to stimulate cell proliferation. In particular, HCDR may be added to a cell or cells in vivo using delivery mechanisms such as liposomes, viral based vectors, or electroinjection for the purpose of promoting regeneration or cell differentiation of the cell or cells. In addition, HCDR may be added to a cell, cell line, tissue or organ culture in vitro or ex vivo to stimulate cell proliferation for use in heterologous or autologous transplantation. In some cases, the cell will have been selected for its ability to fight an infection or a cancer or to correct a genetic defect in a disease such as sickle cell anemia, βthalassemia, cystic fibrosis, or Huntington's chorea.

In another further embodiment, an agonist which is specific for HCDR may be administered to a cell to stimulate cell proliferation, as described above.

In another further embodiment, a vector capable of expressing HCDR, or a fragment or a derivative thereof, may be administered to a cell or cells in vivo using delivery mechanisms, or to a cell to stimulate cell proliferation, as described above.

Increased expression of HCDR appears to be associated with increased cell proliferation. Therefore, in one embodiment, an antagonist of HCDR, or a fragment or a derivative thereof, may be administered to a subject to prevent or treat a disorder associated with cell proliferation. Such disorders include various types of cancer including, but not limited to, adenocarcinoma, leukemia, lymphoma, melanoma, myeloma, sarcoma, and teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody specific for HCDR may be used directly as an antagonist, or indirectly as a targeting or delivery mechanism for bringing a pharmaceutical agent to cells or tissue which express HCDR.

In still another embodiment, a vector expressing the complement of the polynucleotide encoding HCDR, or a fragment or a derivative thereof, may be administered to a subject to prevent or treat a disorder associated with cell proliferation including, but not limited to, the types of cancer listed above.

In another embodiment, an antagonist of HCDR, or a fragment or a derivative thereof, may be administered to a subject to prevent or treat an inflammation. Disorders associated with inflammation include, but are not limited to, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, flugal, parasitic, protozoal, and helminthic infections and trauma. In one aspect, an antibody specific for HCDR may be used directly as an antagonist, or indirectly as a targeting or delivery mechanism for bringing a pharmaceutical agent to cells or tissue which express HCDR.

In still another embodiment, a vector expressing the complement of the polynucleotide encoding HCDR, or a fragment or a derivative thereof, may be administered to a subject to prevent or treat an inflammation associated with any disorder including, but not limited to, those listed above.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HCDR may be produced using methods which are generally known in the art. In particular, purified HCDR may be used to produce antibodies or to screen libraries of pharmaceutical agents to identify those which specifically bind HCDR.

Antibodies to HCDR may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HCDR or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HCDR have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of HCDR amino acids may be fused with those of another protein such as keyhole limpet hemocyanin and antibody produced against the chimeric molecule.

Monoclonal antibodies to HCDR may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; Cole, S. P. et al. (1984) Mol. Cell Biol. 62:109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81:6851–6855; Neuberger, M. S. et al. (1984) Nature 312:604–608; Takeda, S. et al. (1985) Nature 314:452–454). Alternatively, techniques described for the production of single chain antibodies may be adapted, using methods known in the art, to produce HCDR-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349:293–299).

Antibody fragments which contain specific binding sites for HCDR may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse, W. D. et al. (1989) Science 254:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HCDR and its specific antibody. A two-site, monoclonal-based immunoassay utilizing monoclonal antibodies reactive to two non-interfering HCDR epitopes is preferred, but a competitive binding assay may also be employed (Maddox, supra).

In another embodiment of the invention, the polynucleotides encoding HCDR, or any fragment or complement thereof, may be used for therapeutic purposes. In one aspect, the complement of the polynucleotide encoding HCDR may be used in situations in which it would be desirable to block the transcription of the mRNA. In particular, cells may be transformed with sequences complementary to polynucleotides encoding HCDR. Thus, complementary molecules or fragments may be used to modulate HCDR activity, or to achieve regulation of gene function. Such technology is now well known in the art, and sense or antisense oligonucleotides or larger fragments, can be designed from various locations along the coding or control regions of sequences encoding HCDR.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding HCDR. These techniques are described both in Sambrook et al. (supra) and in Ausubel et al. (supra).

Genes encoding HCDR can be turned off by transforming a cell or tissue with expression vectors which express high levels of a polynucleotide or fragment thereof which encodes HCDR. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding HCDR (signal sequence, promoters, enhancers, and introns). Oligonucleotides derived from the transcription initiation site, e.g., between positions −10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HCDR.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HCDR. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15:462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HCDR, antibodies to HCDR, mimetics, agonists, antagonists, or inhibitors of HCDR. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HCDR, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HCDR or fragments thereof, antibodies of HCDR, agonists, antagonists or inhibitors of HCDR, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HCDR may be used for the diagnosis of conditions or diseases characterized by expression of HCDR, or in assays to monitor patients being treated with HCDR, agonists, antagonists or inhibitors. The antibodies useful for diagnostic purposes may be prepared in the same manner as those described above for therapeutics. Diagnostic assays for HCDR include methods which utilize the antibody and a label to detect HCDR in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HCDR are known in the art and provide a basis for diagnosing altered or abnormal levels of HCDR expression. Normal or standard values for HCDR expression are established by combining body fluids or cell extracts taken from normal mammalian subjects, preferably human, with antibody to HCDR under conditions suitable for complex formation The amount of standard complex formation may be quantified by various methods, but preferably by photometric, means. Quantities of HCDR expressed in subject, control and disease, samples from biopsied tissues are compared with the standard values. Deviation between standard and subject values establishes the parameters for diagnosing disease.

In another embodiment of the invention, the polynucleotides encoding HCDR may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HCDR may be correlated with disease. The diagnostic assay may be used to distinguish between absence, presence, and excess expression of HCDR, and to monitor regulation of HCDR levels during therapeutic intervention.

In one aspect, hybridization with PCR probes which are capable of detecting polynucleotide sequences, including genomic sequences, encoding HCDR or closely related molecules, may be used to identify nucleic acid sequences which encode HCDR. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HCDR, alleles, or related sequences.

Probes may also be used for the detection of related sequences, and should preferably contain at least 50% of the nucleotides from any of the HCDR encoding sequences. The hybridization probes of the subject invention may be DNA or RNA and derived from the nucleotide sequence of SEQ ID NO:2, SEQ ID NO:4, SEQ ID NO:6, or from genomic sequence including promoter, enhancer elements, and introns of the naturally occurring HCDR.

Means for producing specific hybridization probes for DNAs encoding HCDR include the cloning of nucleic acid sequences encoding HCDR or HCDR derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HCDR may be used for the diagnosis of conditions or disorders which are associated with expression of HCDR. Examples of such conditions or disorders include, but are not limited to, disorders associated with cell proliferation such as adenocarcinoma, leukemia, lymphoma, melanoma, myeloma, sarcoma, and teratocarcinoma, and particularly, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; disorders with associated inflammation such as Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis; complications of cancer, hemodialysis, extracorporeal circulation; viral, bacterial, fungal, parasitic, protozoal, and helminthic infections and trauma; disorders with associated apoptosis such as AIDS and other infectious or genetic immunodeficiencies, neurodegenerative diseases such as Alzheimer's disease, Parkinson's disease, amyotrophic lateral sclerosis, retinitis pigmentosa, and cerebellar degeneration, myelodysplastic syndromes such as aplastic anemia, ischemic injuries such as myocardial infarction, stroke, and reperfusion injury, toxin-induced diseases such as alcohol-induced liver damage, cirrhosis, and lathyrism, wasting diseases such as cachexia, viral infections such as those caused by hepatitis B and C, and osteoporosis. The polynucleotide sequences encoding HCDR may be used in Southern or northern analysis, dot blot, or other membrane-based technologies; in PCR technologies; or in dipstick, pin, ELISA assays or microarrays utilizing fluids or tissues from patient biopsies to detect altered HCDR expression. Such qualitative or quantitative methods are well known in the art.

In a particular aspect, the nucleotide sequences encoding HCDR may be useful in assays that detect activation or induction of various cancers, particularly those mentioned above. The nucleotide sequences encoding HCDR may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HCDR in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HCDR, a normal or standard profile for expression is established. This may be accomplished by combining body fluids or cell extracts taken from normal subjects, either animal or human, with a sequence, or a fragment thereof, which encodes HCDR, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HCDR may involve the use of PCR. Such oligomers may be chemically synthesized, generated enzymatically, or produced in vitro. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HCDR include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, an oligonucleotide derived from any of the polynucleotide sequences described herein may be used as a target in a microarray. The microarray can be used to monitor the expression level of large numbers of genes simultaneously (to produce a transcript image), and to identify genetic variants, mutations and polymorphisms. This information will be useful in determining gene function, understanding the genetic basis of disease, diagnosing disease, and in developing and monitoring the activity of therapeutic agents (Heller, R. et al. (1997) Proc. Natl. Acad. Sci. 94:2150–55).

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples.

In another embodiment of the invention, the nucleic acid sequences which encode HCDR may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7:127–134, and Trask, B. J. (1991) Trends Genet. 7:149–154.

Fluorescent in situ hybridization (FISH as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding HCDR on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HCDR, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HCDR and the agent being tested, may be measured.

Another technique for drug screening which may be used provides for high throughput screening of compounds having suitable binding affinity to the protein of interest as described in published PCT application WO84/03564. In this method, as applied to HCDR large numbers of different small test compounds are synthesized on a solid substrate, such as plastic pins or some other surface. The test compounds are reacted with HCDR, or fragments thereof, and washed. Bound HCDR is then detected by methods well known in the art. Purified HCDR can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HCDR specifically compete with a test compound for binding HCDR. In this manner, the antibodies can be used to detect the presence of any peptide which shares one or more antigenic determinants with HCDR.

In additional embodiments, the nucleotide sequences which encode HCDR may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I cDNA Library Construction

The human spleen cell cDNA library, SPLNFET01, was custom constructed by Stratagene. The tissue for the SPLNFET01 library was obtained from fetal spleens pooled from different sources and contained many different types of cells. The tissue for Poly(A+) RNA (mRNA) was purified, and cDNA was synthesized from the mRNA. Synthetic adaptor oligonucleotides were ligated onto cDNA ends enabling its insertion into Uni-ZAP™ vector system (Stratagene), allowing high efficiency unidirectional (sense orientation) lambda library construction and the convenience of a plasmid system with blue/white color selection to detect clones with cDNA insertions. Alternative unidirectional vectors are pcDNA1 (Invitrogen, San Diego Calif.) and pSHlox-1 (Novagen, Madison Wis.).

The custom-constructed library phage particles were transfected into E. coli host strain XL1-Blue® (Stratagene), which has a high transformation efficiency, increasing the probability of obtaining rare, under-represented clones in the cDNA library.

The LVENNOT01 cDNA library was constructed from the left ventricle of a 51-year-old Caucasian female. The tissue was frozen, ground, and lysed immediately in buffer containing guanidinium isothiocyanate and spun through cesium chloride. The precipitate was treated by several phenol chloroform extractions and ethanol precipitations at pH 8. The resulting sample was DNased, and the polyadenylated mRNA was then isolated and purified using Qiagen Oligotex (Qiagen, Chatsworth, Calif.).

First strand cDNA synthesis was accomplished using an oligo d(T) primer/linker which also contained an XhoI restriction site. Second strand synthesis was performed using a combination of DNA polymerase I, E. coli ligase, and RNase H, followed by the addition of an EcoRI adaptor to the blunt ended cDNA. The EcoRI adapted, double-stranded cDNA was then digested with XhoI restriction enzyme and fractionated to obtain sequences which exceeded 800 bp in size. The cDNAs were inserted into the LambdaZap® vector system (Stratagene). The vector which contained the pBluescript™ phagemid (Stratagene) was then transformed into E. coli host cells strain XL1-BlueMRF® (Stratagene).

The ENDANOT01 cDNA library was constructed from an aortic endothelial cell line derived from explanted heart/aorta tissue obtained from a male. The frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. RNA extraction and precipitation were repeated as before. The mRNA was then isolated using the Qiagen Oligotex kit (QIAGEN) and used to construct the cDNA libraries.

The mRNA was handled according to the recommended protocols in the SuperScript Plasmid System for cDNA Synthesis and Plasmid Cloning (Cat. #18248-013, Gibco/BRL). cDNAs were fractionated on a SEPHAROSE CL4B column (Cat. #275105-01, Pharmacia), and those cDNAs exceeding 400 bp were ligated into pINCY 1. The plasmid pINCY 1 was subsequently transformed into DH5α competent cells (Cat. #18258-012, Gibco/BRL).

II Isolation and Sequencing of cDNA Clones

The phagemid forms of individual cDNA clones for SPLNFET01 or LVENNOT01 were obtained by the in vivo excision process, in which the host bacterial strain was coinfected with both the lambda library phage and an f1 helper phage. Proteins derived from both the library-containing phage and the helper phage nicked the lambda DNA, initiated new DNA synthesis from defined sequences on the lambda target DNA and created a smaller, single stranded circular phagemid DNA molecule that included all DNA sequences of the pBluescript® plasmid and the cDNA insert. The phagemid DNA was secreted from the cells and purified, then used to re-infect fresh host cells, where the double stranded phagemid DNA was produced. Because the phagemid carries the gene for β-lactamase, the newly-transformed bacteria were selected on medium containing ampicillin.

Phagemid DNA was purified using the QIAwell-8 Plasmid, QIAwell PLUS, or QIAwell ULTRA DNA purification system (QIAGEN). This product line provides a convenient, rapid and reliable high-throughput method to lyse bacterial cells and isolate highly purified phagemid DNA using QIAGEN anion-exchange resin particles with EMPORE membrane technology (3M, Minneapolis, Minn.) in a multiwell format. The DNA was eluted from the purification resin already prepared for DNA sequencing and other analytical manipulations.

Plasmid cDNA for ENDANOT01 was released from the cells and purified using the REAL Prep 96 Plasmid Kit (Catalog #26173, QIAGEN). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced according to the method of Sanger et al. (1975, J. Mol. Biol. 94:441f), using the Perkin Elmer Catalyst 800 or a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems or the Perkin Elmer 373 DNA Sequencing System and the reading frame was determined.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul SF (1993) J. Mol. Evol. 36:290–300; Altschul, SF et al. (1990) J. Mol. Biol. 215:403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith R F and T F Smith (1992 Protein Engineering 5:35–51), incorporated herein by reference, can be used when dealing with primary sequence patterns and secondary structure gap penalties. As disclosed in this application, the sequences have lengths of at least 49 nucleotides, and no more than 12% uncalled bases (where N is recorded rather than A, C, G, or T).

The BLAST approach, as detailed in Karlin and Altschul (1993; Proc Nat Acad Sci 90:5873–7) and incorporated herein by reference, searches matches between a query sequence and a database sequence, to evaluate the statistical significance of any matches found, and to report only those matches which satisfy the user-selected threshold of significance. In this application, threshold was set at $10^{-25}$ for nucleotides and $10^{-14}$ for peptides.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. (1993) J. Mol. Evol. 36:290–300; Altschul, S. F. et al. (1990) J. Mol. Evol. 215:403–410) are used to search for identical or related molecules in nucleotide databases such as GenBank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

% sequence identity×% maximum BLAST score/100

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HCDR occurs. Abundance and percent abundance are also reported. Abundance directly reflects the number of times a particular transcript is represented in a cDNA library, and percent abundance is abundance divided by the total number of sequences examined in the cDNA library.

V Extension of HCDR Encoding Polynucleotides

The nucleic acid sequence of the Incyte Clones 26459, 348429, or 2458438 was used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human cDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture was analyzed by electrophoresis on a low concentration (about 0.6–0.8%)

agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent E. coli cells (in 40 µl of appropriate media) were transformed with 3 µl of ligation mixture and cultured in 80 µl of SOC medium (Sambrook et al., supra). After incubation for one hour at 37° C., the E. coli mixture was plated on Luria Bertani (LB)-agar (Sambrook et al., supra) containing 2× Carb. The following day, several colonies were randomly picked from each plate and cultured in 150 µl of liquid LB/2× Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2, SEQ ID NO:4, or SEQ ID NO:6 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2, SEQ ID NO:4, or SEQ ID NO:6 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [γ-$^{32}$P] adenosine triphosphate (Amersham) and T4 polynucleotide kinase (DuPont NEN, Boston, Mass.). The labeled oligonucleotides are substantially purified with SEPHADEX G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, EcoRI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1× saline sodium citrate and 0.5% sodium dodecyl sulfate. After XOMAT AR film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, at least one of the nucleotide sequences described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J. D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the HCDR-encoding sequence, or any part thereof, is used to decrease or inhibit expression of naturally occurring HCDR. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of HCDR, SEQ ID NO:1, SEQ ID NO:3, or SEQ ID NO:5. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HCDR-encoding transcript.

IX Expression of HCDR

Expression of HCDR is accomplished by subcloning the cDNAs into appropriate vectors and transforming the vectors into host cells. In this case, the cloning vector is also used to express HCDR in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HCDR into the bacterial growth media which can be used directly in the following assay for activity.

X Demonstration of HCDR Activity

HCDR can be expressed by transforming a mammalian cell line such as COS7, HeLa or CHO with an eukaryotic expression vector encoding HCDR. Eukaryotic expression vectors are commercially available, and the techniques to introduce them into cells are well known to those skilled in the art. The cells are incubated for 48–72 hours after transformation under conditions appropriate for the cell line to allow expression of HCDR. Then, phase microscopy is used to compare the mitotic index of transformed versus control cells. An increase in the mitotic index indicates HCDR activity.

XI Production of HCDR Specific Antibodies

HCDR that is substantially purified using PAGE electrophoresis (Sambrook, supra), or other purification techniques, is used to immunize rabbits and to produce antibodies using standard protocols. The amino acid sequence deduced from SEQ ID NO:2, SEQ ID NO:4, or SEQ ID NO:6 is analyzed using LASERGENE software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431 A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat anti-rabbit IgG.

XII Purification of Naturally Occurring HCDR Using Specific Antibodies

Naturally occurring or recombinant HCDR is substantially purified by immunoaffinity chromatography using antibodies specific for HCDR. An immunoaffinity column is constructed by covalently coupling HCDR antibody to an activated chromatographic resin, such as CNBr-activated SEPHAROSE (Pharmacia & Upjohn). After the coupling, the resin is blocked and washed according to the manufacturer's instructions.

Media containing HCDR is passed over the immunoaffinity column, and the column is washed under conditions that allow the preferential absorbance of HCDR (e.g., high ionic strength buffers in the presence of detergent). The column is eluted under conditions that disrupt antibody/HCDR binding (eg, a buffer of pH 2–3 or a high concentration of a chaotrope, such as urea or thiocyanate ion), and HCDR is collected.

XIII Identification of Molecules Which Interact with HCDR

HCDR or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HCDR, washed and any wells with labeled HCDR complex are assayed. Data obtained using different concentrations of HCDR are used to calculate values for the number, affinity, and association of HCDR with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide fragment encoding the human cell division regulator of SEQ ID No:5.

2. A composition comprising the polynucleotide fragment of claim 1.

3. An isolated and purified polynucleotide fragment which is completely complementary to the polynucleotide fragment of claim 1.

4. An isolated and purified polynucleotide fragment comprising the polynucleotide of SEQ ID No:6.

5. A composition comprising the polynucleotide fragment of claim 4.

6. An isolated and purified polynucleotide fragment which is completely complementary to the polynucleotide fragment of claim 4.

7. An expression vector comprising the polynucleotide fragment of claim 4.

8. A host cell comprising the expression vector of claim 4.

9. A method for producing a polypeptide comprising the amino acid sequence of SEQ ID No:5, the method comprising the steps of:

a) culturing the host cell of claim 8 under conditions suitable for the expression of the polypeptide; and b) recovering the polypeptide from the host cell culture.

10. A method for detecting a polynucleotide which encodes a human cell division regulator in a biological sample, the method comprising the steps of:

a) hybridizing the polynucleotide of claim 3 to nucleic acid material in the biological sample, thereby forming a hybridization complex; and b) detecting the hybridization complex, wherein the presence of the hybridization complex correlates with the presence of a polynucleotide encoding the human cell division regulator in the biological sample.

11. The method of claim 10 wherein the nucleic acid material is amplified by the polymerase chain reaction prior to hybridization.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 478 amino acids
      (B) TYPE: amino acid
      (C) STRANDEDNESS: single
      (D) TOPOLOGY: linear (vii) IMMEDIATE SOURCE:
      (A) LIBRARY: SPLNFZT01
      (B) CLONE: 26459

(xi) SEQUENCE DESCRIPTION: SEQ ID NO:1:

-continued

```
Met Asp Arg Ser Leu Gly Trp Gln Gly Asn Ser Val Pro Glu Asp Arg
 1               5                   10                  15

Thr Glu Ala Gly Ile Lys Arg Phe Leu Glu Asp Thr Thr Asp Asp Gly
            20                  25                  30

Glu Leu Ser Lys Phe Val Lys Asp Phe Ser Gly Asn Ala Ser Cys His
        35                  40                  45

Pro Pro Glu Ala Lys Thr Trp Ala Ser Arg Pro Gln Val Pro Glu Pro
 50                  55                  60

Arg Pro Gln Ala Pro Asp Leu Tyr Asp Asp Leu Glu Phe Arg Pro
 65                  70                  75                  80

Pro Ser Arg Pro Gln Ser Ser Asp Asn Gln Gln Tyr Phe Cys Ala Pro
                85                  90                  95

Ala Pro Leu Ser Pro Ser Ala Arg Pro Arg Ser Pro Trp Gly Lys Leu
             100                 105                 110

Asp Pro Tyr Asp Ser Ser Glu Asp Asp Lys Glu Tyr Val Gly Phe Ala
             115                 120                 125

Thr Leu Pro Asn Gln Val His Arg Lys Ser Val Lys Lys Gly Phe Asp
     130                 135                 140

Phe Thr Leu Met Val Ala Gly Glu Ser Gly Leu Gly Lys Ser Thr Leu
 145                 150                 155                 160

Val Asn Ser Leu Phe Leu Ser Asp Leu Tyr Arg Asp Arg Lys Leu Leu
             165                 170                 175

Gly Ala Glu Glu Arg Ile Met Gln Thr Val Glu Ile Thr Lys His Ala
             180                 185                 190

Val Asp Ile Glu Glu Lys Gly Val Arg Leu Arg Leu Thr Ile Val Asp
             195                 200                 205

Thr Pro Gly Phe Gly Asp Ala Val Asn Asn Thr Glu Cys Trp Lys Pro
     210                 215                 220

Val Ala Glu Tyr Ile Asp Gln Gln Phe Glu Gln Tyr Phe Arg Asp Glu
 225                 230                 235                 240

Ser Gly Leu Asn Arg Lys Asn Ile Gln Asp Asn Arg Val His Cys Cys
             245                 250                 255

Leu Tyr Phe Ile Ser Pro Phe Gly His Gly Leu Arg Pro Leu Asp Val
             260                 265                 270

Glu Phe Met Lys Ala Leu His Gln Arg Val Asn Ile Val Pro Ile Leu
             275                 280                 285

Ala Lys Ala Asp Thr Leu Thr Pro Pro Glu Val Asp His Lys Lys Arg
     290                 295                 300

Lys Ile Arg Glu Glu Ile Glu His Phe Gly Ile Lys Ile Tyr Gln Phe
 305                 310                 315                 320

Pro Asp Cys Asp Ser Asp Glu Asp Glu Asp Phe Lys Leu Gln Asp Gln
             325                 330                 335

Ala Leu Lys Glu Ser Ile Pro Phe Ala Val Ile Gly Ser Asn Thr Val
     340                 345                 350

Val Glu Ala Arg Gly Arg Arg Val Arg Gly Arg Leu Tyr Pro Trp Gly
             355                 360                 365

Ile Val Glu Val Glu Asn Pro Gly His Cys Asp Phe Val Lys Leu Arg
     370                 375                 380

Thr Met Leu Val Arg Thr His Met Gln Asp Leu Lys Asp Val Thr Arg
 385                 390                 395                 400

Glu Thr His Tyr Glu Asn Tyr Arg Ala Gln Cys Ile Gln Ser Met Thr
             405                 410                 415

Arg Leu Val Val Lys Glu Arg Asn Arg Asn Lys Leu Thr Arg Glu Ser
```

```
                  420             425             430
Gly Thr Asp Phe Pro Ile Pro Ala Val Pro Pro Gly Thr Asp Pro Glu
            435             440             445

Thr Glu Lys Leu Ile Arg Glu Lys Asp Glu Glu Leu Arg Arg Met Gln
    450             455             460

Glu Met Leu His Lys Ile Gln Lys Gln Met Lys Glu Asn Tyr
465             470             475

(2) INFORMATION FOR SEQ ID NO:2:

(i) SEQUENCE CHARACTERISTICS:
        (A) LENGTH: 1816 base pairs
        (B) TYPE: nucleic acid
        (C) STRANDEDNESS: single
        (D) TOPOLOGY: linear (vii) IMMEDIATE SOURCE:
        (A) LIBRARY: SPLNFZT01
        (B) CLONE: 26459

(xi) SEQUENCE DESCRIPTION: SEQ ID NO:2:

TGGGGTGGGG AAGGACATTC ACAGGCTTTT TTTGGCCCCT GCCAGAGACA GAAGGGGGTC       60

AAAGAGAAAG GGAAAGGAGC AAGCCAGGAA GCCAGACAAC AACAGCATCA AAACAAGGCT      120

GTTTCTGTGT GTGAGGAACT TTGCCTGGGA GATAAAATTA GACCTAGAGC TTTCTGACAG      180

GGAGTCTGAA GCGTGGGACA TGGACCGTTC ACTGGGATGG CAAGGGAATT CTGTCCCTGA      240

GGACAGGACT GAAGCTGGGA TCAAGCGTTT CCTGGAGGAC ACCACGGATG ATGGAGAACT      300

GAGCAAGTTC GTGAAGGATT TCTCAGGAAA TGCGAGCTGC CACCCACCAG AGGCTAAGAC      360

CTGGGCATCC AGGCCCCAAG TCCCGGAGCC AAGGCCCCAG GCCCCGGACC TCTATGATGA      420

TGACCTGGAG TTCAGACCCC CCTCGCGGCC CCAGTCCTCT GACAACCAGC AGTACTTCTG      480

TGCCCCAGCC CCTCTCAGCC CATCTGCCAG GCCCCGCAGC CCATGGGCA AGCTTGATCC       540

CTATGATTCC TCTGAGGATG ACAAGGAGTA TGTGGGCTTT GCAACCCTCC CCAACCAAGT      600

CCACCGAAAG TCCGTGAAGA AAGGCTTTGA CTTTACCCTC ATGGTGGCAG AGAGTCTGG      660

CCTGGGCAAA TCCACACTTG TCAATAGCCT CTTCCTCTCT GATCTGTACC GGGACCGGAA      720

ACTTCTTGGT GCTGAAGAGA GGATCATGCA AACTGTGGAG ATCACTAAGC ATGCAGTGGA      780

CATAGAAGAG AAGGGTGTGA GGCTGCGGCT CACCATTGTG GACACACCAG GTTTTGGGGA      840

TGCAGTCAAC AACACAGAGT GCTGGAAGCC TGTGGCAGAA TACATTGATC AGCAGTTTGA      900

GCAGTATTTC CGAGACGAGA GTGGCCTGAA CCGAAAGAAC ATCCAAGACA CAGGGTGCA      960

CTGCTGCCTG TACTTCATCT CACCCTTCGG CCATGGGCTC CGGCCATTGG ATGTTGAATT     1020

CATGAAGGCC CTGCATCAGC GGGTCAACAT CGTGCCTATC CTGGCTAAGG CAGACACACT     1080

GACACCTCCC GAAGTGGACC ACAAGAAACG CAAAATCCGG GAGGAGATTG AGCATTTTGG     1140

AATCAAGATC TATCAATTCC CAGACTGTGA CTCTGATGAG GATGAGGACT TCAAATTGCA     1200

GGACCAAGCC CTAAAGGAAA GCATCCCATT TGCAGTAATT GGCAGCAACA CTGTAGTAGA     1260

GGCCAGAGGG CGGCGAGTTC GGGGTCGACT CTACCCCTGG GGCATCGTGG AAGTGGAAAA     1320

CCCAGGGCAC TGCGACTTTG TGAAGCTGAG GACAATGCTG GTACGTACCC ACATGCAGGA     1380

CCTGAAGGAT GTGACACGGG AGACACATTA TGAGAACTAC CGGGCACAGT GCATCCAGAG     1440

CATGACCCGC CTGGTGGTGA AGGAACGGAA TCGCAACAAA CTGACTCGGG AAAGTGGTAC     1500

CGACTTCCCC ATCCCTGCTG TCCCACCAGG GACAGATCCA GAAACTGAGA AGCTTATCCG     1560

AGAGAAAGAT GAGGAGCTGC GGCGGATGCA GGAGATGCTA CACAAAATAC AAAAACAGAT     1620
```

```
GAAGGAGAAC TATTAACTGG CTTTCAGCCC TGGATATTTA AATCTCCTCC TCTTCTTCCT      1680

GTCCATGCCG GCCCCTCCCA GCACCAGCTC TGCTCAGGCC CCTTCAGCTA CTGCCACTTC      1740

GCCTTACATC CCTGCTGACT GCCCAGAGAC TCAGAGGAAA TAAAGTTTAA TAAATCTGTA      1800

GGTGGCAAAA AAAAAA                                                     1816
```

(2) INFORMATION FOR SEQ ID NO:3:

(i) SEQUENCE CHARACTERISTICS:
        (A) LENGTH: 425 amino acids
        (B) TYPE: amino acid
        (C) STRANDEDNESS: single
        (D) TOPOLOGY: linear (vii) IMMEDIATE SOURCE:
        (A) LIBRARY: LVZNNOT01
        (B) CLONE: 348429

(xi) SEQUENCE DESCRIPTION: SEQ ID NO:3:

```
Met Ala Val Ala Val Gly Arg Pro Ser Asn Glu Glu Leu Arg Asn Leu
 1               5                  10                  15

Ser Leu Ser Gly His Val Gly Phe Asp Ser Leu Pro Asp Gln Leu Val
            20                  25                  30

Asn Lys Ser Thr Ser Gln Gly Phe Cys Phe Asn Ile Leu Cys Val Gly
        35                  40                  45

Glu Thr Gly Ile Gly Lys Ser Thr Leu Met Asp Thr Leu Phe Asn Thr
50                  55                  60

Lys Phe Glu Ser Asp Pro Ala Thr His Asn Glu Pro Gly Val Arg Leu
65                  70                  75                  80

Lys Ala Arg Ser Tyr Glu Leu Gln Glu Ser Asn Val Arg Leu Lys Leu
                85                  90                  95

Thr Ile Val Asp Thr Val Gly Phe Gly Asp Gln Ile Asn Lys Asp Asp
            100                 105                 110

Ser Tyr Lys Pro Ile Val Glu Tyr Ile Asp Ala Gln Phe Glu Ala Tyr
        115                 120                 125

Leu Gln Glu Glu Leu Lys Ile Lys Arg Ser Leu Phe Asn Tyr His Asp
    130                 135                 140

Thr Arg Ile His Ala Cys Leu Tyr Phe Ile Ala Pro Thr Gly His Ser
145                 150                 155                 160

Leu Lys Ser Leu Asp Leu Val Thr Met Lys Lys Leu Asp Ser Lys Val
                165                 170                 175

Asn Ile Ile Pro Ile Ile Ala Lys Ala Asp Thr Ile Ala Lys Asn Glu
            180                 185                 190

Leu His Lys Phe Lys Ser Lys Ile Met Ser Glu Leu Val Ser Asn Gly
        195                 200                 205

Val Gln Ile Tyr Gln Phe Pro Thr Asp Glu Glu Thr Val Ala Glu Ile
    210                 215                 220

Asn Ala Thr Met Ser Val His Leu Pro Phe Ala Val Val Gly Ser Thr
225                 230                 235                 240

Glu Glu Val Lys Ile Gly Asn Lys Met Ala Lys Ala Arg Gln Tyr Pro
                245                 250                 255

Trp Gly Val Val Gln Val Glu Asn Glu Asn His Cys Asp Phe Val Lys
            260                 265                 270

Leu Arg Glu Met Leu Ile Arg Val Asn Met Glu Asp Leu Arg Glu Gln
        275                 280                 285

Thr His Thr Arg His Tyr Glu Leu Tyr Arg Arg Cys Lys Leu Glu Glu
```

```
            290                 295                 300
Met Gly Phe Lys Asp Thr Asp Pro Asp Ser Lys Pro Phe Ser Leu Gln
305                 310                 315                 320

Glu Thr Tyr Glu Ala Lys Arg Asn Glu Phe Leu Gly Glu Leu Gln Lys
                325                 330                 335

Lys Glu Glu Glu Met Arg Gln Met Phe Val Met Arg Val Lys Glu Lys
            340                 345                 350

Glu Ala Glu Leu Lys Glu Ala Glu Lys Glu Leu His Glu Lys Phe Asp
        355                 360                 365

Leu Leu Lys Arg Thr His Gln Glu Lys Lys Lys Val Glu Asp Lys
370                 375                 380

Lys Lys Glu Leu Glu Glu Val Asn Asn Phe Gln Lys Lys Lys Ala
385                 390                 395                 400

Ala Ala Gln Leu Leu Gln Ser Gln Ala Gln Gln Ser Gly Ala Gln Gln
                405                 410                 415

Thr Lys Lys Asp Lys Asp Lys Lys Asn
                420                 425

(2) INFORMATION FOR SEQ ID NO:4:

(i) SEQUENCE CHARACTERISTICS:
        (A) LENGTH: 1794 base pairs
        (B) TYPE: nucleic acid
        (C) STRANDEDNESS: single
        (D) TOPOLOGY: linear (vii) IMMEDIATE SOURCE:
        (A) LIBRARY: LVZNNOT01
        (B) CLONE: 348429

(xi) SEQUENCE DESCRIPTION: SEQ ID NO:4:

GAGGCGCGAG GGAGGCGAGC CGGAGCCCGA GCACTAGCAG CAGCCGGAGT CGGCGGAAAG     60

CACCCGGGCG CACGGNAGAC GGTGCCGCAG CTGCGATGGC CGTGGCCGTG GGGAGACCGT    120

CTAATGAAGA GCTTCGAAAC TTGTCTTTGT CTGGCCATGT GGGATTTGAC AGCCTCCCTG    180

ACCAGCTGGT CAACAAGTCT ACTTCTCAAG GATTCTGTTT CAACATCCTT TGTGTTGGTG    240

AGACAGGCAT TGGCAAATCC ACGTTAATGG ACACTTTGTT CAACACCAAA TTTGAAAGTG    300

ACCCAGCTAC TCACAATGAA CCAGGTGTTC GGTTAAAAGC CAGAAGTTAT GAGCTTCAGG    360

AAAGCAATGT ACGGCTGAAG TTAACCATTG TTGACACCGT GGGATTTGGA GACCAGATAA    420

ATAAAGATGA CAGCTATAAG CCGATAGTAG AATATATTGA TGCCCAGTTC GAGGCCTACC    480

TGCAAGAGGA ATTGAAGATT AAACGTTCTC TCTTCAACTA CCATGACACG AGGATCCATG    540

CCTGCCTCTA CTTTATTGCC CCTACTGGAC ATTCACTAAA GTCCCTGGAT CTGGTCACCA    600

TGAAAAAGCT GGACAGTAAG GTGAACATCA TTCCAATAAT TGCAAAAGCT GACACCATTG    660

CCAAGAATGA ACTGCACAAA TTCAAGAGTA AGATCATGAG TGAACTGGTC AGCAATGGGG    720

TCCAGATATA TCAGTTTCCC ACTGATGAAG AAACGGTGGC AGAGATTAAC GCAACAATGA    780

GTGTCCATCT CCCATTTGCA GTGGTTGGCA GCACCGAAGA GGTGAAGATT GGCAACAAGA    840

TGGCAAAGGC CAGGCAGTAC CCCTGGGGTG TGGTGCAGGT TGAGAATGAA AATCATTGCG    900

ATTTTGTGAA ACTTCGAGAG ATGCTGATCC GCGTGAACAT GGAGGACTTG CGAGAGCAGA    960

CTCACACCCG CCACTATGAA TTGTACCGAC GCTGTAAGCT TGAAGAGATG GGGTTCAAGG   1020

ACACTGACCC TGACAGCAAA CCCTTCAGTC TTCAGGAGAC ATATGAAGCA AAAAGGAATG   1080

AATTCCTGGG AGAACTGCAG AAGAAAGAAG AAGAAATGAG ACAAATGTTT GTTATGAGAG   1140
```

-continued

```
TGAAGGAGAA AGAAGCTGAA CTTAAGGAGG CAGAGAAAGA GCTTCACGAG AAGTTTGACC    1200

TTCTAAAGCG GACACACCAA GAAGAAAAGA AGAAAGTGGA AGACAAGAAG AAGGAGCTTG    1260

AGGAGGAGGT GAACAACTTC CAGAAGAAGA AAGCAGCGGC TCAGTTACTA CAGTCCCAGG    1320

CCCAGCAATC TGGGGCCCAG CAAACCAAGA AAGACAAGGA TAAGAAAAAC TGACCATCTG    1380

CCTCTTGAGA GAGAGAGAAG TGGGCATCCT TCCTTTAAAT TCAGGAACCA CTGTTGTTTT    1440

ATTTGACTTT TTCTGTTACT TGCATCCCTT ATATAAGTTG TTTTGGATTT GGGACTATGT    1500

TTTGGGGGAG AAAAACTCCA GTTAGTTCTG TTTTTTGTAT TGGTTATTCA GCTTACTTTT    1560

GGTATCAAAA TTATGCCAGT TTTAAGCTCA CTTGAGTGAA GTTTAAGTCA CAAGATTCTG    1620

TTTAACATGC TTTCCTTGTT TTGGAAACAA CCAAAAACTT CCCTTTTTTG TTACGGGATT    1680

TTGACCTACA AATCCTAATC ATGTTTAAAA TGTGCCGGTG TTGGGTAGAT GACTTTCTG     1740

CCTCTGGGGT TCAATTTATA TTTAAAGATA CCTTAAAATA AAAAAAAAAG AAAA          1794
```

(2) INFORMATION FOR SEQ ID NO:5:

(i) SEQUENCE CHARACTERISTICS:
        (A) LENGTH: 394 amino acids
        (B) TYPE: amino acid
        (C) STRANDEDNESS: single
        (D) TOPOLOGY: linear (vii) IMMEDIATE SOURCE:
        (A) LIBRARY: ZNDANOT01
        (B) CLONE: 2458438

(xi) SEQUENCE DESCRIPTION: SEQ ID NO:5:

```
Met Ser Gly Glu Asp Glu Gln Gln Glu Gln Thr Ile Ala Glu Asp Leu
 1               5                  10                  15

Val Val Thr Lys Tyr Lys Met Gly Gly Asp Ile Ala Asn Arg Val Leu
            20                  25                  30

Arg Ser Leu Val Glu Ala Ser Ser Gly Val Ser Val Leu Ser Leu
        35                  40                  45

Cys Glu Lys Gly Asp Ala Met Ile Met Glu Glu Thr Gly Lys Ile Phe
    50                  55                  60

Lys Lys Glu Lys Glu Met Lys Lys Gly Ile Ala Phe Pro Thr Ser Ile
65                  70                  75                  80

Ser Val Asn Asn Cys Val Cys His Phe Ser Pro Leu Lys Ser Asp Gln
                85                  90                  95

Asp Tyr Ile Leu Lys Glu Gly Asp Leu Val Lys Ile Asp Leu Gly Val
            100                 105                 110

His Val Asp Gly Phe Ile Ala Asn Val Ala His Thr Phe Val Val Asp
        115                 120                 125

Val Ala Gln Gly Thr Gln Val Thr Gly Arg Lys Ala Asp Val Ile Lys
    130                 135                 140

Ala Ala His Leu Cys Ala Glu Ala Ala Leu Arg Leu Val Lys Pro Gly
145                 150                 155                 160

Asn Gln Asn Thr Gln Val Thr Glu Ala Trp Asn Lys Val Ala His Ser
                165                 170                 175

Phe Asn Cys Thr Pro Ile Glu Gly Met Leu Ser His Gln Leu Lys Gln
            180                 185                 190

His Val Ile Asp Gly Glu Lys Thr Ile Ile Gln Asn Pro Thr Asp Gln
        195                 200                 205

Gln Lys Lys Asp His Glu Lys Ala Glu Phe Glu Val His Glu Val Tyr
    210                 215                 220
```

-continued

```
Ala Val Asp Val Leu Val Ser Ser Gly Glu Gly Lys Ala Lys Asp Ala
225                 230                 235                 240

Gly Gln Arg Thr Thr Ile Tyr Lys Arg Asp Pro Ser Lys Gln Tyr Gly
            245                 250                 255

Leu Lys Met Lys Thr Ser Arg Ala Phe Phe Ser Glu Val Glu Arg Arg
            260                 265                 270

Phe Asp Ala Met Pro Phe Thr Leu Arg Ala Phe Glu Asp Glu Lys Lys
        275                 280                 285

Ala Arg Met Gly Val Val Glu Cys Ala Lys His Glu Leu Leu Gln Pro
290                 295                 300

Phe Asn Val Leu Tyr Glu Lys Gly Glu Phe Val Ala Gln Phe Lys
305                 310                 315                 320

Phe Thr Val Leu Leu Met Pro Asn Gly Pro Met Arg Ile Thr Ser Gly
            325                 330                 335

Pro Phe Glu Pro Asp Leu Tyr Leu Ser Glu Met Glu Val Gln Asp Ala
            340                 345                 350

Glu Leu Lys Ala Leu Leu Gln Ser Ser Ala Ser Arg Lys Thr Gln Lys
            355                 360                 365

Lys Lys Lys Lys Lys Ala Ser Lys Thr Ala Glu Asn Ala Thr Ser Gly
        370                 375                 380

Glu Thr Leu Glu Glu Asn Glu Ala Gly Asp
385                 390
```

(2) INFORMATION FOR SEQ ID NO:6:

(i) SEQUENCE CHARACTERISTICS:
        (A) LENGTH: 1456 base pairs
        (B) TYPE: nucleic acid
        (C) STRANDEDNESS: single
        (D) TOPOLOGY: linear (vii) IMMEDIATE SOURCE:
        (A) LIBRARY: ZNDANOT01
        (B) CLONE: 2458438

(xi) SEQUENCE DESCRIPTION: SEQ ID NO:6:

```
TGCGCCTCAG CCCGCGCGCT CGCAGCTTCT CGCTCTCGCC TGCCTGCCCG CTCCCTTGCT      60

TGCTCGCGCT TTCGCTCGCC CTCTCCTCGA GGATCGAGGG GACTCTGACC ACAGCCTGTG     120

GCTGGGAAGG GAGACAGAGG CGGCGGCGGC TCAGGGAAA CGAGGCTGCA GTGGTGGTAG      180

TAGGAAGATG TCGGGCGAGG ACGAGCAACA GGAGCAAACT ATCGCTGAGG ACCTGGTCGT     240

GACCAAGTAT AAGATGGGGG GCGACATCGC CAACAGGGTA CTTCGGTCCT TGGTGGAAGC     300

ATCTAGCTCA GGTGTGTCGG TATTGAGCCT GTGTGAGAAA GGTGATGCCA TGATTATGGA     360

AGAAACAGGG AAAATCTTCA GAAAGAAAA GGAAATGAAG AAAGGTATTG CTTTTCCCAC      420

CAGCATTTCG GTAAATAACT GTGTATGTCA CTTCTCCCCT TTGAAGAGCG ACCAGGATTA     480

TATTCTCAAG GAAGGTGACT TGGTAAAAAT TGACCTTGGG GTCCATGTGG ATGGCTTCAT     540

CGCTAATGTA GCTCACACTT TTGTGGTTGA TGTAGCTCAG GGGACCCAAG TAACAGGGAG     600

GAAAGCAGAT GTTATTAAGG CAGCTCACCT TTGTGCTGAA GCTGCCCTAC GCCTGGTCAA     660

ACCTGGAAAT CAGAACACAC AAGTGACAGA AGCCTGGAAC AAAGTTGCCC ACTCATTTAA     720

CTGCACGCCA ATAGAAGGTA TGCTGTCACA CCAGTTGAAG CAGCATGTCA TCGATGGAGA     780

AAAAACCATT ATCCAGAATC CCACAGACCA GCAGAAGAAG GACCATGAAA AAGCTGAATT     840

TGAGGTACAT GAAGTATATG CTGTGGATGT TCTCGTCAGC TCAGGAGAGG GCAAGGCCAA     900

GGATGCAGGA CAGAGAACCA CTATTTACAA ACGAGACCCC TCTAAACAGT ATGGACTGAA     960
```

-continued

```
AATGAAAACT TCACGTGCCT TCTTCAGTGA GGTGGAAAGG CGTTTTGATG CCATGCCGTT     1020

TACTTTAAGA GCATTTGAAG ATGAGAAGAA GGCTCGGATG GGTGTGGTGG AGTGCGCCAA     1080

ACATGAACTG CTGCAACCAT TTAATGTTCT CTATGAGAAG GAGGGTGAAT TTGTTGCCCA     1140

GTTTAAATTT ACAGTTCTGC TCATGCCCAA TGGCCCCATG CGGATAACCA GTGGTCCCTT     1200

CGAGCCTGAC CTCTACAAGT CTGAGATGGA GGTCCAGGAT GCAGAGCTAA AGGCCCTCCT     1260

CCAGAGTTCT GCAAGTCGAA AAACCCAGAA AAGAAAAAA  AAGAAGGCCT CCAAGACTGC     1320

AGAGAATGCC ACCAGTGGGG AAACATTAGA AGAAAATGAA GCTGGGGACT GAGGTGGGTC     1380

CCATCTCCCC AGCTTGCTGC TCCTGCCTCA TCCCCTTCCC ACCATACCCC AGACTCTGTG     1440

AAGGCAGTTT TTCTCC                                                    1456
```

(2) INFORMATION FOR SEQ ID NO:7:

(i) SEQUENCE CHARACTERISTICS:
        (A) LENGTH: 478 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 51203

(xi) SEQUENCE DESCRIPTION: SEQ ID NO:7:

```
Met Asp His Ser Leu Gly Trp Gln Gly Asn Ser Val Pro Glu Asp Gly
  1               5                  10                  15

Thr Glu Ala Gly Ile Lys His Phe Leu Glu Asp Ser Ser Asp Asp Ala
             20                  25                  30

Glu Leu Ser Lys Phe Val Lys Asp Phe Pro Gly Ser Glu Pro Tyr His
         35                  40                  45

Ser Ala Glu Ser Lys Thr Arg Val Ala Arg Pro Gln Ile Leu Glu Pro
     50                  55                  60

Arg Pro Gln Ser Pro Asp Leu Cys Asp Asp Val Glu Phe Arg Gly
 65                  70                  75                  80

Ser Leu Trp Pro Gln Pro Ser Asp Ser Gln Gln Tyr Phe Ser Ala Pro
                 85                  90                  95

Ala Pro Leu Ser Pro Ser Ser Arg Pro Arg Ser Pro Trp Gly Lys Leu
            100                 105                 110

Asp Pro Tyr Asp Ser Ser Glu Asp Lys Glu Tyr Val Gly Phe Ala
        115                 120                 125

Thr Leu Pro Asn Gln Val His Arg Lys Ser Val Lys Lys Gly Phe Asp
    130                 135                 140

Phe Thr Leu Met Val Ala Gly Glu Ser Gly Leu Gly Lys Ser Thr Leu
145                 150                 155                 160

Val Asn Ser Leu Phe Leu Thr Asp Leu Tyr Arg Asp Arg Lys Leu Leu
                165                 170                 175

Gly Ala Glu Glu Arg Ile Met Gln Thr Val Glu Ile Thr Lys His Ala
            180                 185                 190

Val Asp Ile Glu Glu Lys Gly Val Arg Leu Arg Leu Thr Ile Val Asp
        195                 200                 205

Thr Pro Gly Phe Gly Asp Ala Val Asn Asn Thr Glu Cys Trp Lys Pro
    210                 215                 220

Val Ala Glu Tyr Ile Asp Gln Gln Phe Glu Gln Tyr Phe Arg Asp Glu
225                 230                 235                 240
```

-continued

```
Ser Gly Leu Asn Arg Lys Asn Ile Gln Asp Asn Arg Val His Cys Cys
                245                 250                 255

Leu Tyr Phe Ile Ser Pro Phe Gly His Gly Leu Arg Pro Leu Asp Val
            260                 265                 270

Glu Phe Met Lys Ala Leu His Gln Arg Val Asn Ile Val Pro Ile Leu
        275                 280                 285

Ala Lys Ala Asp Thr Leu Thr Pro Pro Glu Val Asp Arg Lys Lys Cys
290                 295                 300

Lys Ile Arg Glu Glu Ile Glu His Phe Gly Ile Lys Ile Tyr Gln Phe
305                 310                 315                 320

Pro Asp Cys Asp Ser Asp Glu Asp Glu Asp Phe Lys Leu Gln Asp Gln
                325                 330                 335

Ala Leu Lys Glu Ser Ile Pro Phe Ala Val Ile Gly Ser Asn Thr Val
            340                 345                 350

Val Glu Ala Arg Gly Arg Arg Val Arg Gly Arg Leu Tyr Pro Trp Gly
        355                 360                 365

Ile Val Glu Val Glu Asn Pro Gly His Cys Asp Phe Val Lys Leu Arg
370                 375                 380

Thr Met Leu Val Arg Thr His Met Gln Asp Leu Lys Asp Val Thr Arg
385                 390                 395                 400

Glu Thr His Tyr Glu Asn Tyr Arg Ala Gln Cys Ile Gln Ser Met Thr
                405                 410                 415

Arg Leu Val Val Lys Glu Arg Asn Arg Asn Lys Leu Thr Arg Glu Ser
            420                 425                 430

Gly Thr Asp Phe Pro Ile Pro Ala Val Pro Pro Gly Thr Asp Pro Glu
        435                 440                 445

Thr Glu Lys Leu Ile Arg Glu Lys Asp Glu Glu Leu Arg Arg Met Gln
450                 455                 460

Glu Met Leu His Lys Ile Gln Arg Gln Met Lys Glu Thr His
465                 470                 475

(2) INFORMATION FOR SEQ ID NO:8:

(i) SEQUENCE CHARACTERISTICS:
        (A) LENGTH: 369 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1829317

(xi) SEQUENCE DESCRIPTION: SEQ ID NO:8:

Met Ser Thr Gly Leu Arg Tyr Lys Ser Lys Leu Ala Thr Pro Glu Asp
1               5                   10                  15

Lys Gln Asp Ile Asp Lys Gln Tyr Val Gly Phe Ala Thr Leu Pro Asn
            20                  25                  30

Gln Val His Arg Lys Ser Val Lys Lys Gly Phe Asp Phe Thr Leu Met
        35                  40                  45

Val Ala Gly Glu Ser Gly Leu Gly Lys Ser Thr Leu Val His Ser Leu
50                  55                  60

Phe Leu Thr Asp Leu Tyr Lys Asp Arg Lys Leu Leu Ser Ala Glu Glu
65                  70                  75                  80

Arg Ile Ser Gln Thr Val Glu Ile Leu Lys His Thr Val Asp Ile Glu
                85                  90                  95

Glu Lys Gly Val Lys Leu Lys Leu Thr Ile Val Asp Thr Pro Gly Phe
```

-continued

```
                100                 105                 110
Gly Asp Ala Val Asn Asn Thr Glu Cys Trp Lys Pro Ile Thr Asp Tyr
            115                 120                 125
Val Asp Gln Gln Phe Glu Gln Tyr Phe Arg Asp Glu Ser Gly Leu Asn
        130                 135                 140
Arg Lys Asn Ile Gln Asp Asn Arg Val His Cys Cys Leu Tyr Phe Ile
145                 150                 155                 160
Ser Pro Phe Gly His Gly Leu Arg Pro Val Asp Val Gly Phe Met Lys
                165                 170                 175
Ala Leu His Glu Lys Val Asn Ile Val Pro Leu Ile Ala Lys Ala Asp
            180                 185                 190
Cys Leu Val Pro Ser Glu Ile Arg Lys Leu Lys Glu Arg Ile Arg Glu
        195                 200                 205
Glu Ile Asp Lys Phe Gly Ile His Val Tyr Gln Phe Pro Glu Cys Asp
    210                 215                 220
Ser Asp Glu Asp Glu Asp Phe Lys Gln Gln Asp Arg Glu Leu Lys Glu
225                 230                 235                 240
Ser Ala Pro Phe Ala Val Ile Gly Ser Asn Thr Val Val Glu Ala Lys
                245                 250                 255
Gly Gln Arg Val Arg Gly Arg Leu Tyr Pro Trp Gly Ile Val Glu Val
            260                 265                 270
Glu Asn Gln Ala His Cys Asp Phe Val Lys Leu Arg Asn Met Leu Ile
        275                 280                 285
Arg Thr His Met His Asp Leu Lys Asp Val Thr Cys Asp Val His Tyr
    290                 295                 300
Glu Asn Tyr Arg Ala His Cys Ile Gln Gln Met Thr Ser Lys Leu Thr
305                 310                 315                 320
Gln Asp Ser Arg Met Glu Ser Pro Ile Pro Ile Leu Pro Leu Pro Thr
                325                 330                 335
Pro Asp Ala Glu Thr Glu Lys Leu Ile Arg Met Lys Asp Glu Glu Leu
            340                 345                 350
Arg Arg Met Gln Glu Met Leu Gln Arg Met Lys Gln Gln Met Gln Asp
        355                 360                 365
Gln
```

(2) INFORMATION FOR SEQ ID NO:9:

(i) SEQUENCE CHARACTERISTICS:
  (A) LENGTH: 424 amino acids
  (B) TYPE: amino acid
  (C) STRANDEDNESS: single
  (D) TOPOLOGY: linear (vii) IMMEDIATE SOURCE:
  (A) LIBRARY: GenBank
  (B) CLONE: 1469179

(xi) SEQUENCE DESCRIPTION: SEQ ID NO:9:

```
Thr Asp Ile Ala Arg Gln Val Gly Glu Gly Cys Arg Thr Val Pro Leu
1               5                   10                  15
Ala Gly His Val Gly Phe Asp Ser Leu Pro Asp Gln Leu Val Asn Lys
                20                  25                  30
Ser Val Ser Gln Gly Phe Cys Phe Asn Ile Leu Cys Val Gly Glu Thr
            35                  40                  45
Gly Leu Gly Lys Ser Thr Leu Met Asp Thr Leu Phe Asn Thr Lys Phe
        50                  55                  60
```

Glu Gly Glu Pro Ala Thr His Thr Gln Pro Gly Val Gln Leu Gln Ser
65                  70                  75                  80

Asn Thr Tyr Asp Leu Gln Glu Ser Asn Val Arg Leu Lys Leu Thr Ile
                85                  90                  95

Val Ser Thr Val Gly Phe Gly Asp Gln Ile Asn Lys Glu Asp Ser Tyr
            100                 105                 110

Lys Pro Ile Val Glu Phe Ile Asp Ala Gln Phe Glu Ala Tyr Leu Gln
        115                 120                 125

Glu Glu Leu Lys Ile Arg Arg Val Leu His Thr Tyr His Asp Ser Arg
    130                 135                 140

Ile His Val Cys Leu Tyr Phe Ile Ala Pro Thr Gly His Ser Leu Lys
145                 150                 155                 160

Ser Leu Asp Leu Val Thr Met Lys Lys Leu Asp Ser Lys Val Asn Ile
                165                 170                 175

Ile Pro Ile Ile Ala Lys Ala Asp Ala Ile Ser Lys Ser Glu Leu Thr
            180                 185                 190

Lys Phe Lys Ile Lys Ile Thr Ser Glu Leu Val Ser Asn Gly Val Gln
        195                 200                 205

Ile Tyr Gln Phe Pro Thr Asp Asp Glu Ser Val Ala Glu Ile Asn Gly
    210                 215                 220

Thr Met Asn Ala His Leu Pro Phe Ala Val Ile Gly Ser Thr Glu Glu
225                 230                 235                 240

Leu Lys Ile Gly Asn Lys Met Met Arg Ala Arg Gln Tyr Pro Trp Gly
                245                 250                 255

Thr Val Gln Val Glu Asn Glu Ala His Cys Asp Phe Val Lys Leu Arg
            260                 265                 270

Glu Met Leu Ile Arg Val Asn Met Glu Asp Leu Arg Glu Gln Thr His
        275                 280                 285

Thr Arg His Tyr Glu Leu Tyr Arg Arg Cys Lys Leu Glu Glu Met Gly
    290                 295                 300

Phe Lys Asp Thr Asp Pro Asp Ser Lys Pro Phe Ser Leu Gln Glu Thr
305                 310                 315                 320

Tyr Glu Ala Lys Arg Asn Glu Phe Leu Gly Glu Leu Gln Lys Lys Glu
                325                 330                 335

Glu Glu Met Arg Gln Met Phe Val Gln Arg Val Lys Glu Lys Glu Ala
            340                 345                 350

Glu Leu Lys Glu Ala Glu Lys Glu Leu His Glu Lys Phe Asp Arg Leu
        355                 360                 365

Lys Lys Leu His Gln Asp Glu Lys Lys Leu Glu Asp Lys Lys Lys
370                 375                 380

Ser Leu Asp Asp Glu Val Asn Ala Phe Lys Gln Arg Lys Thr Ala Ala
385                 390                 395                 400

Glu Leu Leu Gln Ser Gln Gly Ser Gln Ala Gly Gly Ser Gln Thr Leu
                405                 410                 415

Lys Arg Asp Lys Glu Lys Lys Asn
            420

(2) INFORMATION FOR SEQ ID NO:10:

(i) SEQUENCE CHARACTERISTICS:
        (A) LENGTH: 394 amino acids
        (B) TYPE: amino acid
        (C) STRANDEDNESS: single
        (D) TOPOLOGY: linear (vii) IMMEDIATE SOURCE:

(A) LIBRARY: GenBank
(B) CLONE: 1167967

(xi) SEQUENCE DESCRIPTION: SEQ ID NO:10:

```
Met Ser Gly Glu Asp Glu Gln Glu Gln Thr Ile Ala Glu Asp Leu
 1               5                  10                  15

Val Val Thr Lys Tyr Lys Met Gly Gly Asp Ile Ala Asn Arg Val Leu
             20                  25                  30

Arg Ser Leu Val Glu Ala Ser Ser Gly Val Ser Val Leu Ser Leu
             35                  40                  45

Cys Glu Lys Gly Asp Ala Met Ile Met Glu Glu Thr Gly Lys Ile Phe
 50                  55                  60

Lys Lys Glu Lys Glu Met Lys Lys Gly Ile Ala Phe Pro Thr Ser Ile
 65                  70                  75                  80

Ser Val Asn Asn Cys Val Cys His Phe Ser Pro Leu Lys Ser Asp Gln
                 85                  90                  95

Asp Tyr Ile Leu Lys Glu Gly Asp Leu Val Lys Ile Asp Leu Gly Val
                100                 105                 110

His Val Asp Gly Phe Ile Ala Asn Val Ala His Thr Phe Val Ile Gly
            115                 120                 125

Val Ala Gln Gly Thr Gln Val Thr Gly Arg Lys Ala Asp Val Ile Lys
130                 135                 140

Ala Ala His Leu Cys Ala Glu Ala Leu Arg Leu Val Lys Pro Gly
145                 150                 155                 160

Asn Gln Asn Thr Gln Val Thr Glu Ala Trp Asn Lys Val Ala His Ser
                165                 170                 175

Phe Asn Cys Thr Pro Ile Glu Gly Met Leu Ser His Gln Leu Lys Gln
            180                 185                 190

His Val Ile Asp Gly Glu Lys Thr Ile Ile Gln Asn Pro Thr Asp Gln
            195                 200                 205

Gln Lys Lys Asp His Glu Lys Ala Glu Phe Glu Val His Glu Val Tyr
    210                 215                 220

Ala Val Asp Val Leu Val Ser Ser Gly Glu Gly Lys Ala Lys Asp Ala
225                 230                 235                 240

Gly Gln Arg Thr Thr Ile Tyr Lys Arg Asp Pro Ser Lys Gln Tyr Gly
                245                 250                 255

Leu Lys Met Lys Thr Ser Arg Ala Phe Phe Ser Glu Val Glu Arg Arg
            260                 265                 270

Phe Asp Ala Met Pro Phe Thr Leu Arg Ala Phe Glu Asp Glu Lys Lys
            275                 280                 285

Ala Arg Met Gly Val Val Glu Cys Ala Lys His Glu Leu Leu Gln Pro
290                 295                 300

Phe Asn Val Leu Tyr Glu Lys Glu Gly Glu Phe Val Ala Gln Phe Lys
305                 310                 315                 320

Phe Thr Val Leu Leu Met Pro Asn Gly Pro Met Arg Ile Thr Ser Gly
                325                 330                 335

Pro Phe Glu Pro Asp Leu Tyr Lys Ser Glu Met Glu Val Gln Asp Ala
            340                 345                 350

Glu Leu Lys Ala Leu Leu Gln Ser Ser Ala Ser Arg Lys Thr Gln Lys
            355                 360                 365
```

―continued

```
Lys Lys Lys Lys Lys Ala Ser Lys Thr Val Glu Asn Ala Thr Ser Gly
    370                 375                 380

Glu Thr Leu Glu Glu Asn Gly Ala Gly Asp
385                 390
```